(12) United States Patent
Kaiser et al.

(10) Patent No.: US 9,445,025 B2
(45) Date of Patent: *Sep. 13, 2016

(54) SYSTEM, METHOD, AND PRODUCT FOR IMAGING PROBE ARRAYS WITH SMALL FEATURE SIZES

(71) Applicants: Michael D. Kaiser, Natick, MA (US); David R. Smith, San Jose, CA (US)

(72) Inventors: Michael D. Kaiser, Natick, MA (US); David R. Smith, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,959

(22) Filed: Aug. 23, 2013

(65) Prior Publication Data

US 2015/0057167 A1    Feb. 26, 2015

Related U.S. Application Data

(63) Continuation of application No. 13/241,970, filed on Sep. 23, 2011, now Pat. No. 8,520,976, which is a continuation of application No. 11/627,876, filed on Jan. 26, 2007, now Pat. No. 8,055,098.

(60) Provisional application No. 60/762,621, filed on Jan. 27, 2006.

(51) Int. Cl.
| | |
|---|---|
| *G06K 9/32* | (2006.01) |
| *H04N 5/372* | (2011.01) |
| *G06T 5/00* | (2006.01) |
| *G06T 3/40* | (2006.01) |
| *G06T 5/50* | (2006.01) |
| *G01N 21/64* | (2006.01) |

(52) U.S. Cl.
CPC ............ *H04N 5/372* (2013.01); *G06T 3/4069* (2013.01); *G06T 5/003* (2013.01); *G06T 5/50* (2013.01); *G01N 21/6452* (2013.01); *G06T 2207/10056* (2013.01); *G06T 2207/10148* (2013.01); *G06T 2207/30072* (2013.01)

(58) Field of Classification Search
None
See application file for complete search history.

(56) References Cited

U.S. PATENT DOCUMENTS

| | | | |
|---|---|---|---|
| 2,886,241 | A | 5/1959 | Spaulding et al. |
| 3,216,313 | A | 11/1965 | Chisholm |
| 3,385,160 | A | 5/1968 | Dawson et al. |
| 3,632,212 | A | 1/1972 | Bernal |

(Continued)

FOREIGN PATENT DOCUMENTS

| | | |
|---|---|---|
| EP | 0254644 | 1/1988 |
| EP | 0380659 | 8/1990 |

(Continued)

OTHER PUBLICATIONS

Alexay et al., "Fluorescence scanner employing a Macro Scanning Objective," Progress in Biomedical Optics, SPIE, Proceedings of Fluorescence Detection IV, vol. 2705, pp. 63-72 (1996).

(Continued)

*Primary Examiner* — Randolph I Chu
(74) *Attorney, Agent, or Firm* — Banner & Witcoff, Ltd.

(57) ABSTRACT

An embodiment of a method for resolving features on a probe array is described that, comprises acquiring a plurality of micro-shifted images of a region of a probe array; reconstructing an image of the probe array using the micro-shifted images; and deriving intensity values for one or more probe features disposed on the probe array from the reconstructed image.

21 Claims, 16 Drawing Sheets

(56) References Cited

U.S. PATENT DOCUMENTS

| | | |
|---|---|---|
| 3,798,449 A | 3/1974 | Reinheimer et al. |
| 3,802,966 A | 4/1974 | Delekto et al. |
| 3,984,171 A | 10/1976 | Hotchkiss |
| 4,016,855 A | 4/1977 | Mimata |
| 4,070,111 A | 1/1978 | Harrick |
| 4,176,925 A | 12/1979 | Kocher et al. |
| 4,180,739 A | 12/1979 | Abu-Shumays |
| 4,204,929 A | 5/1980 | Bier |
| 4,342,905 A | 8/1982 | Fujii et al. |
| 4,417,260 A | 11/1983 | Kawai et al. |
| 4,448,534 A | 5/1984 | Wertz et al. |
| 4,537,861 A | 8/1985 | Elings et al. |
| 4,579,430 A | 4/1986 | Bille |
| 4,580,895 A | 4/1986 | Patel |
| 4,626,684 A | 12/1986 | Landa |
| 4,708,494 A | 11/1987 | Kleinerman |
| 4,772,125 A | 9/1988 | Yoshimura et al. |
| 4,786,170 A | 11/1988 | Groebler |
| 4,810,869 A | 3/1989 | Yabe et al. |
| 4,815,274 A | 3/1989 | Piatti |
| 4,844,617 A | 7/1989 | Kelderman et al. |
| 4,878,971 A | 11/1989 | Tsunekawa et al. |
| 4,963,498 A | 10/1990 | Hillman et al. |
| 5,001,766 A | 3/1991 | Baird |
| 5,061,075 A | 10/1991 | Alfano et al. |
| 5,091,652 A | 2/1992 | Mathies et al. |
| 5,124,102 A | 6/1992 | Serafini et al. |
| 5,132,524 A | 7/1992 | Singh et al. |
| 5,143,854 A | 9/1992 | Pirrung et al. |
| 5,188,963 A | 2/1993 | Stapleton |
| 5,192,980 A | 3/1993 | Dixon et al. |
| 5,198,871 A | 3/1993 | Hill, Jr. et al. |
| 5,200,051 A | 4/1993 | Cozzette et al. |
| 5,214,531 A | 5/1993 | Torii et al. |
| 5,235,180 A | 8/1993 | Montagu |
| 5,281,516 A | 1/1994 | Stapleton et al. |
| 5,300,779 A | 4/1994 | Hillman et al. |
| 5,304,487 A | 4/1994 | Wilding et al. |
| 5,304,810 A | 4/1994 | Amos |
| 5,310,469 A | 5/1994 | Cunningham et al. |
| 5,320,808 A | 6/1994 | Holen et al. |
| 5,346,672 A | 9/1994 | Stapleton et al. |
| 5,371,690 A | 12/1994 | Engel et al. |
| 5,381,224 A | 1/1995 | Dixon |
| 5,382,511 A | 1/1995 | Stapleton |
| 5,384,261 A | 1/1995 | Winkler et al. |
| 5,405,783 A | 4/1995 | Pirrung et al. |
| 5,424,186 A | 6/1995 | Fodor et al. |
| 5,436,129 A | 7/1995 | Stapleton |
| 5,445,934 A | 8/1995 | Fodor et al. |
| 5,451,500 A | 9/1995 | Stapleton |
| 5,459,325 A | 10/1995 | Hueton et al. |
| 5,471,248 A | 11/1995 | Bhargava et al. |
| 5,474,796 A | 12/1995 | Brennan |
| 5,485,530 A | 1/1996 | Lakowicz et al. |
| 5,486,335 A | 1/1996 | Wilding et al. |
| 5,487,115 A | 1/1996 | Surka |
| 5,489,678 A | 2/1996 | Fodor |
| 5,494,124 A | 2/1996 | Dove et al. |
| 5,497,773 A | 3/1996 | Kuhara et al. |
| 5,498,392 A | 3/1996 | Wilding et al. |
| 5,527,681 A | 6/1996 | Holmes |
| 5,532,873 A | 7/1996 | Dixon |
| 5,545,531 A | 8/1996 | Rava et al. |
| 5,565,324 A | 10/1996 | Still et al. |
| 5,571,639 A | 11/1996 | Hubbell et al. |
| 5,572,598 A | 11/1996 | Wihl et al. |
| 5,578,832 A | 11/1996 | Trulson et al. |
| 5,581,487 A | 12/1996 | Kelly et al. |
| 5,583,342 A | 12/1996 | Ichie |
| 5,585,639 A | 12/1996 | Dorsel et al. |
| 5,604,819 A | 2/1997 | Barnard |
| 5,627,912 A | 5/1997 | Matsumoto |
| 5,631,734 A | 5/1997 | Stern et al. |
| 5,646,411 A | 7/1997 | Kain et al. |
| 5,672,880 A | 9/1997 | Kain |
| 5,720,928 A | 2/1998 | Schwartz |
| 5,721,435 A | 2/1998 | Troll |
| 5,733,729 A | 3/1998 | Lipshutz et al. |
| 5,737,121 A | 4/1998 | Dixon et al. |
| 5,741,411 A | 4/1998 | Yeung et al. |
| 5,744,305 A | 4/1998 | Fodor et al. |
| 5,760,951 A | 6/1998 | Dixon et al. |
| 5,800,992 A | 9/1998 | Fodor et al. |
| 5,801,970 A | 9/1998 | Rowland et al. |
| 5,812,272 A | 9/1998 | King et al. |
| 5,825,913 A | 10/1998 | Rostami et al. |
| 5,834,758 A | 11/1998 | Trulson et al. |
| 5,835,620 A | 11/1998 | Kaplan et al. |
| 5,837,475 A | 11/1998 | Dorsel et al. |
| 5,845,001 A | 12/1998 | Thomas et al. |
| 5,845,007 A | 12/1998 | Ohashi et al. |
| 5,858,659 A | 1/1999 | Sapolsky et al. |
| 5,861,242 A | 1/1999 | Chee et al. |
| 5,886,353 A | 3/1999 | Spivey et al. |
| 5,916,747 A | 6/1999 | Gilchrist et al. |
| 5,917,588 A | 6/1999 | Addiego et al. |
| 5,945,334 A | 8/1999 | Besemer et al. |
| 5,981,956 A | 11/1999 | Stern |
| 6,045,996 A | 4/2000 | Cronin et al. |
| 6,066,459 A | 5/2000 | Garini et al. |
| 6,077,674 A | 6/2000 | Schleifer et al. |
| 6,083,763 A | 7/2000 | Balch et al. |
| 6,090,555 A | 7/2000 | Fiekowsky et al. |
| 6,100,030 A | 8/2000 | McCasky |
| 6,122,042 A | 9/2000 | Wunderman et al. |
| 6,124,102 A | 9/2000 | Fodor et al. |
| 6,140,044 A | 10/2000 | Besemer |
| 6,141,096 A | 10/2000 | Stern et al. |
| 6,167,169 A | 12/2000 | Brinkman et al. |
| 6,207,960 B1 | 3/2001 | Stern et al. |
| 6,228,575 B1 | 5/2001 | Gingeras et al. |
| 6,242,266 B1 | 6/2001 | Schleifer et al. |
| 6,284,459 B1 | 9/2001 | Nova et al. |
| 6,284,465 B1 | 9/2001 | Wolber |
| 6,289,382 B1 | 9/2001 | Bowman-Amuah et al. |
| 6,306,599 B1 | 10/2001 | Perbost |
| 6,309,828 B1 | 10/2001 | Schleifer et al. |
| 6,319,674 B1 | 11/2001 | Fulcrand et al. |
| 6,323,043 B1 | 11/2001 | Caren et al. |
| 6,349,144 B1 | 2/2002 | Shams et al. |
| 6,362,832 B1 | 3/2002 | Stephan et al. |
| 6,372,483 B2 | 4/2002 | Schleifer et al. |
| 6,383,742 B1 | 5/2002 | Drmanac et al. |
| 6,399,365 B2 | 6/2002 | Besemer et al. |
| 6,406,849 B1 | 6/2002 | Dorsel et al. |
| 6,465,183 B2 | 10/2002 | Wolber et al. |
| 6,498,863 B1 | 12/2002 | Gaidoukevitch et al. |
| 6,571,005 B1 | 5/2003 | Li et al. |
| 6,587,575 B1 | 7/2003 | Windham et al. |
| 6,591,196 B1 | 7/2003 | Yakhini et al. |
| 6,599,693 B1 | 7/2003 | Webb |
| 6,611,767 B1 | 8/2003 | Fiekowsky et al. |
| 6,613,893 B1 | 9/2003 | Webb |
| 6,731,781 B1 | 5/2004 | Shams et al. |
| 6,741,344 B1 | 5/2004 | Stern et al. |
| 6,768,820 B1 | 7/2004 | Yakhini et al. |
| 6,829,376 B2 | 12/2004 | Bartell |
| 6,963,806 B2 | 11/2005 | Gulati |
| 6,993,173 B2 | 1/2006 | Zuzan |
| 7,003,177 B1 * | 2/2006 | Mendlovic ............ G06T 3/4069 382/299 |
| 7,006,927 B2 | 2/2006 | Yakhini et al. |
| 7,027,629 B2 | 4/2006 | Cattell et al. |
| 7,075,059 B2 | 7/2006 | Oldham et al. |
| 7,145,645 B2 | 12/2006 | Blumenfeld et al. |
| 7,184,610 B2 | 2/2007 | Weinstein et al. |
| 7,217,573 B1 | 5/2007 | Oshida et al. |
| 7,279,338 B2 | 10/2007 | Kim et al. |
| 7,285,384 B2 | 10/2007 | Fan et al. |
| 7,286,164 B2 | 10/2007 | Shinohara et al. |
| 7,317,820 B2 | 1/2008 | Park |
| 7,330,606 B2 | 2/2008 | Yakhini et al. |
| 7,636,636 B2 | 12/2009 | Piper |

(56) References Cited

U.S. PATENT DOCUMENTS

| | | | |
|---|---|---|---|
| 2001/0055764 A1* | 12/2001 | Empedocles et al. | 435/6 |
| 2002/0028521 A1 | 3/2002 | Ogura | |
| 2002/0150935 A1 | 10/2002 | Zhou et al. | |
| 2002/0193962 A1 | 12/2002 | Yakhini et al. | |
| 2003/0137585 A1* | 7/2003 | Mahon | H04N 3/1587 348/135 |
| 2003/0152490 A1 | 8/2003 | Trulson et al. | |
| 2004/0006431 A1 | 1/2004 | Bartell et al. | |
| 2004/0033485 A1 | 2/2004 | Li et al. | |
| 2004/0096854 A1 | 5/2004 | Choong et al. | |
| 2004/0096883 A1 | 5/2004 | Fiekowsky et al. | |
| 2004/0224332 A1 | 11/2004 | Loney | |
| 2004/0239885 A1* | 12/2004 | Jaynes | H04N 9/3147 353/30 |
| 2005/0048566 A1 | 3/2005 | Fredrick | |
| 2005/0049796 A1 | 3/2005 | Webb | |
| 2005/0056768 A1* | 3/2005 | Oldham et al. | 250/208.1 |
| 2005/0239114 A1 | 10/2005 | Ryu et al. | |
| 2005/0239115 A1 | 10/2005 | Ryu et al. | |
| 2006/0194261 A1 | 8/2006 | Kim et al. | |
| 2007/0003155 A1 | 1/2007 | Miller et al. | |
| 2011/0243411 A1 | 10/2011 | Weiner et al. | |

FOREIGN PATENT DOCUMENTS

| | | |
|---|---|---|
| EP | 0695941 | 7/2002 |
| EP | 0923050 | 12/2004 |
| EP | 1162572 | 3/2006 |
| EP | 1345026 | 5/2010 |
| JP | 1-251717 | 10/1989 |
| JP | 6-119431 | 4/1994 |
| WO | WO 84/01031 | 3/1984 |
| WO | WO 90/15070 | 12/1990 |
| WO | WO 92/10092 | 6/1992 |
| WO | WO 92/10588 | 6/1992 |
| WO | WO 93/02992 | 2/1993 |
| WO | WO 93/09668 | 5/1993 |
| WO | WO 95/00530 | 1/1995 |
| WO | WO 95/11995 | 5/1995 |
| WO | WO 99/08233 | 2/1999 |
| WO | WO 01/06395 | 1/2001 |
| WO | WO 01/35080 | 5/2001 |
| WO | WO 01/56216 | 8/2001 |
| WO | WO 03/030620 | 4/2003 |
| WO | WO 03/033126 | 4/2003 |
| WO | WO 03/033742 | 4/2003 |
| WO | WO 03/034064 | 4/2003 |

OTHER PUBLICATIONS

Basarsky et al., "Overview of a microarray scanner: design essentials for an integrated acquisition and analysis platform," Microarray Biochip Technology, pp. 265-284 (2000).

Bassett Jr. et al., "Gene expression informatics—it's all in your mine," Nature America Inc., Nature Genetics Supplement, vol. 21, pp. 51-55 (Jan. 1999).

Benschop et al., "Confocal compact scanning optical microscope based on compact disk technology," Applied Optics, vol. 30, No. 10, pp. 1179-1184 (1991).

Bentley, "The Development and Application of Automated Gridding for Efficient Screening of Yeast and Bacterial Libraries," Genomics, vol. 12, pp. 534-541 (1992).

Chee et al., "Accessing Genetic Information with High-Density DNA Arrays," Science, vol. 274, pp. 610-614 (Oct. 1996).

Cheung and deSilva, "Analysis of Gene Microarray Images," 6th International Conference on Neural Information Processing, vol. 2, pp. 627-632, Nov. 16-19, 1999.

Cowlishaw, "Densely packed decimal encoding," IEE Proc. Comput. Digit. Tech., vol. 149, issue 3, pp. 102-104 (2002).

Dixon et al., "Confocal scanning beam laser microscope/macroscope: applications in fluorescence," Progess in Biomedical Optics, SPIE, Proceedings of Fluorescence Detection IV, vol. 2703, pp. 44-52 (1996).

Eisen, "ScanAlyze User Manual," pp. 1-22, Jul. 14, 1999.

Elkins et al., "Development of microspot multianalyte ratiometric immunoassay using dual-fluorescent-labelled antibodies," Analytica Chimica, ACTA, 227: 73-96 (Dec. 1989).

Ekins et al, "Multianalyte microspot immunoassay-microanalytical compact disk of the future:" Clin. Chem. 37(11): 1955-1967 (Nov. 1991).

Fodor et al., "Light-Directed, Spatially Addressable Parallel Chemical Synthesis," Science, vol. 251 pp. 767-773 (Feb. 1991).

GeneChip Version 1.0 Help Menu File.

GeneChip Version 1.0 HYB&WASH.MAC file, pp. 1-8, Affymetrix, Apr. 18, 1996.

GeneChip Version 1.0a Help Menu File.

GeneChip Version 1.0a HYB&WASH.MAC file, pp. 1-8, Affymetrix, Mar. 28, 1996.

GeneChip Version 2.0 3WStain.MAC file, pp. 1-11, Affymetrix, Dec. 11, 1996.

GeneChip Version 2.0 Help Menu File.

GeneChip Version 2.0 HybWash.mac file, pp. 1-8, Affymetrix, Apr. 18, 1996.

GeneChip Version 2.0 PRT 430a.MAC file, pp. 1-8, Affymetrix, Apr. 18, 1996.

GeneChip Version 2.0 PRT 430s.MAC file, pp. 1-8, Affymetrix, Apr. 18, 1996.

GeneChip Version 2.0 PRT 440a.MAC file, pp. 1-8, Affymetrix, Apr. 18, 1996.

GeneChip Version 2.0 PRT 440s.MAC file, pp. 1-8, Affymetrix, Apr. 18, 1996.

Golub et al., "Matrix Computations," 3rd Edition, The John Hopkins University Press (1996).

Jain, "Fundamentals of Digital image Processing," Prentic Hall, Inc., pp. 381-383 (1989).

Kuklin et al., "High throughput screening of gene expression signatures," Genetica 108, pp. 41-46 (2000).

Lockhart et al., "Expression monitoring by hybridization to high-density oligonucleotide arrays," Nature Biotechnology, vol. 14, No. 13, pp, 1675-1680 (Dec. 1996).

Pease et al., "Light-generated oligonucleotide arrays for rapid DNA sequence analysis," Proc. Natl. Acad. Sci., vol. 91, pp. 5022-5026 (May 1994).

Quesada et al., "High-sensitivity DNA detection with a laser-excited confocal fluorescent gel scanner," Biotechniques, 10:616-625 (1991).

Sapolsky et al., "Mapping Genomic Library Clones Using Oligonucleotide Arrays," Genomics, vol. 33, Article No. 0219, pp. 445-456 (1996).

Stryer, Biochemistry, 2nd Edition, W.H. Freeman and Co., p. 47 (1981).

Van der Voort et al., "Design and use of a computer controlled confocal microscope for biological applications," Scanning, 7:67-78 (1985).

White et al., "An evaluation of confocal versus conventional imaging of biological structures by fluorescent light microscopy," J. Cell. Biol., 105:41-48 (Jul. 1987).

Yamamoto et al., "Features and applications of the laser scanning microscope," Journal of Modern Optics, vol. 37, No. 11, pp. 1691-1701 (1990).

Young et al., "Handbook of Pattern Recognition and Image Processing," Academic Press, Inc., pp. 191-193, 200-201, 203, and 223 (1986).

Zuzan, "Estimating Probe Cell Locations," Institute of Statistics and Decision Sciences, Duke University, Nov. 19, 2001, Affymetrix, Inc., Data Analysis Workshop.

* cited by examiner

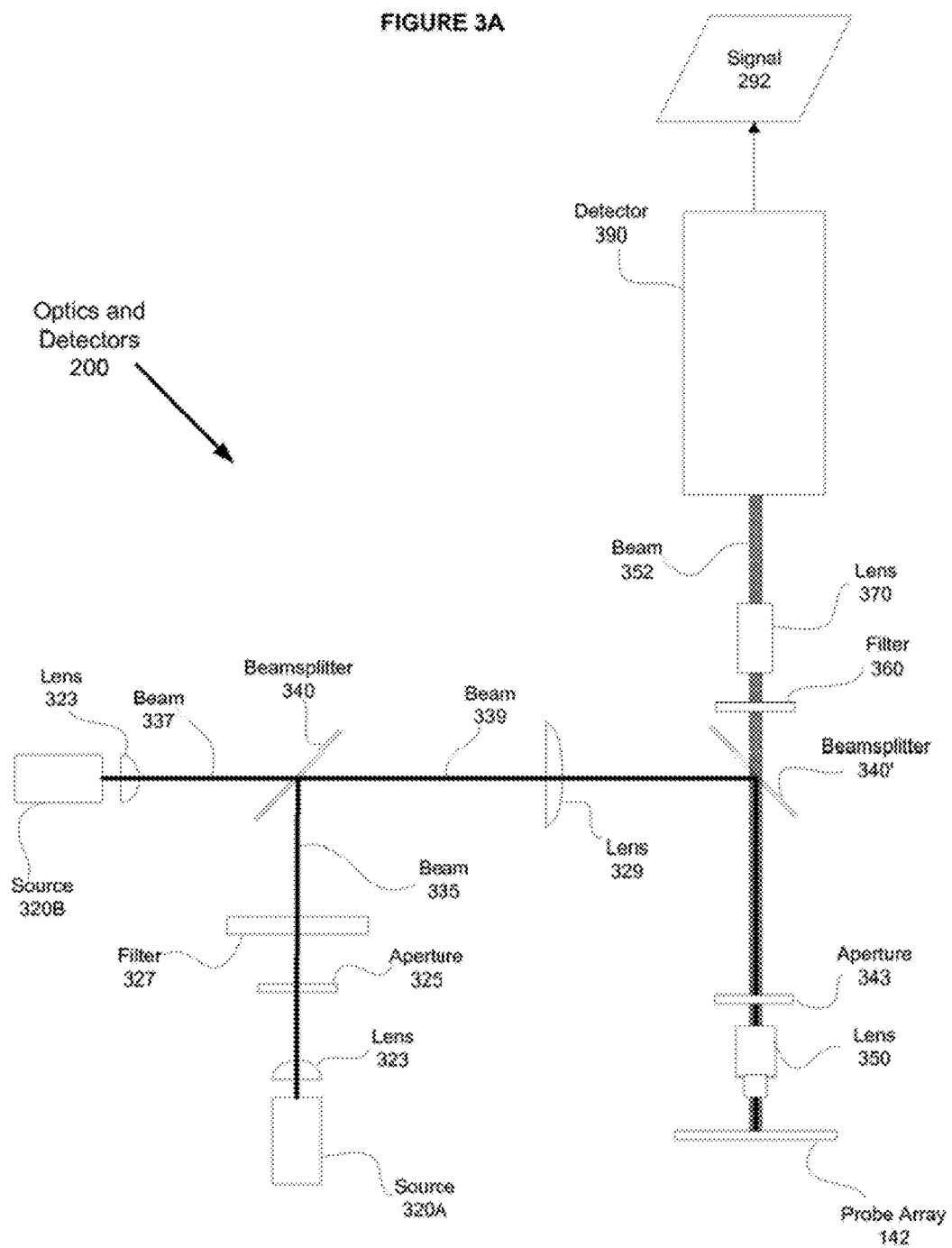

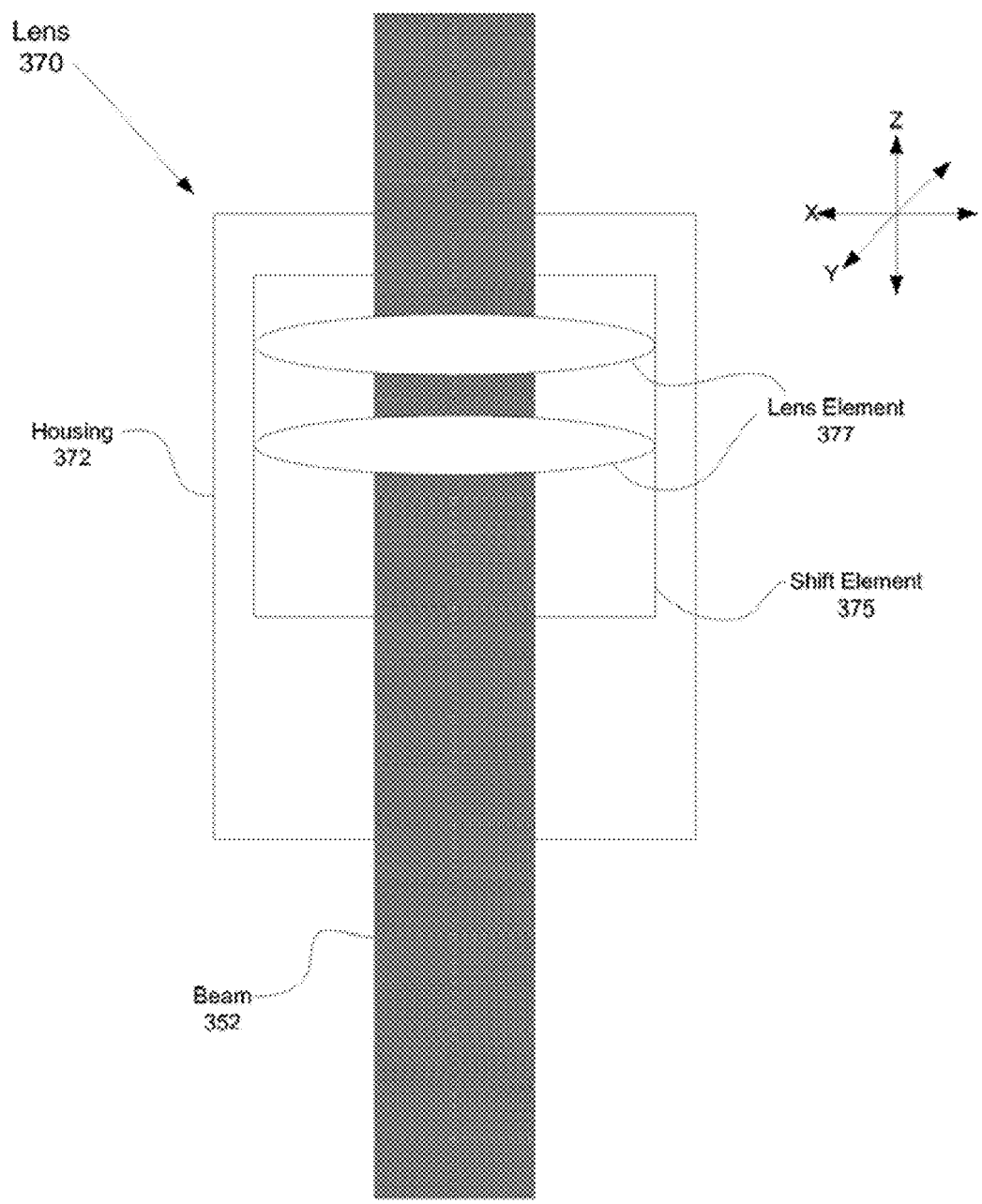

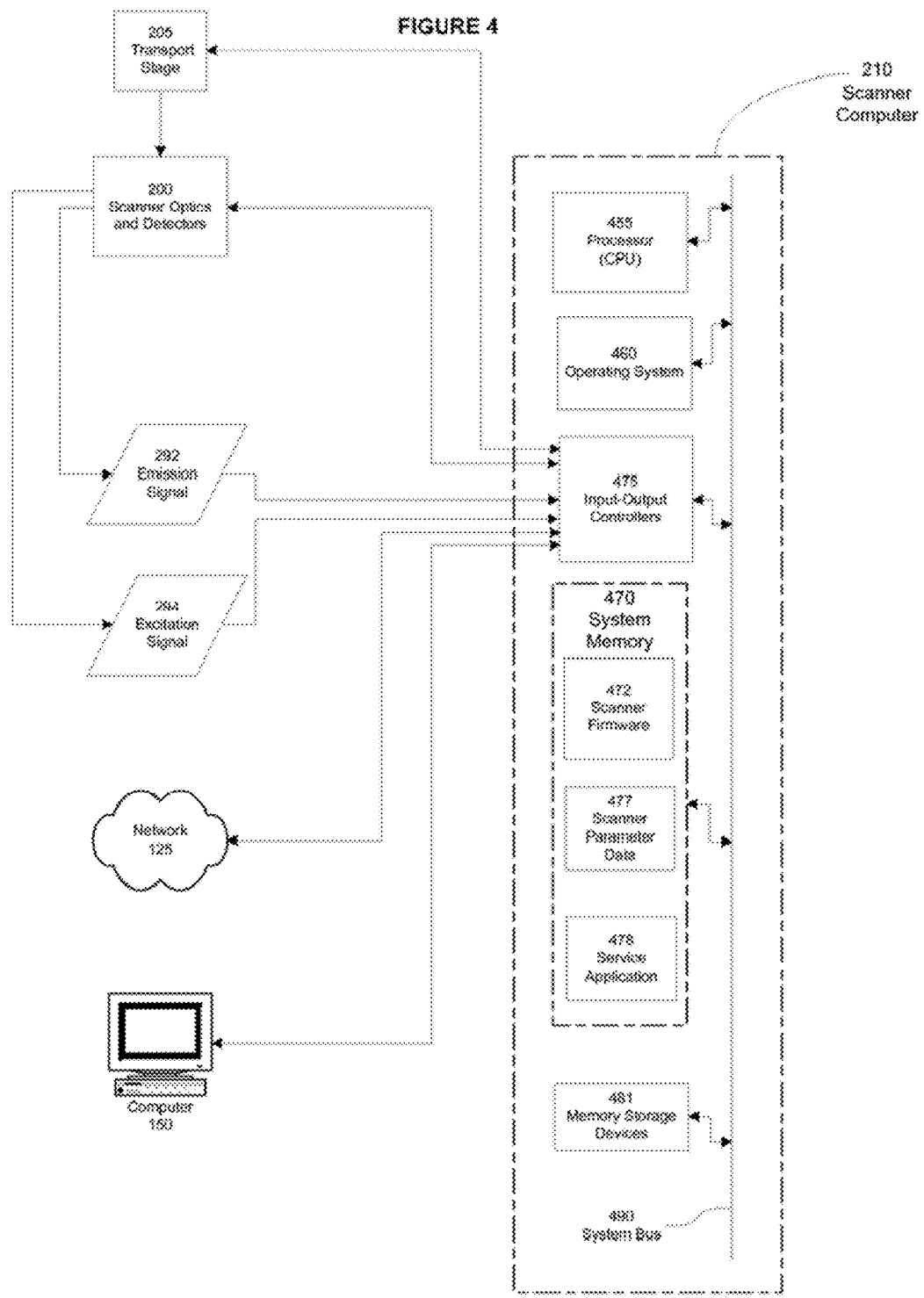

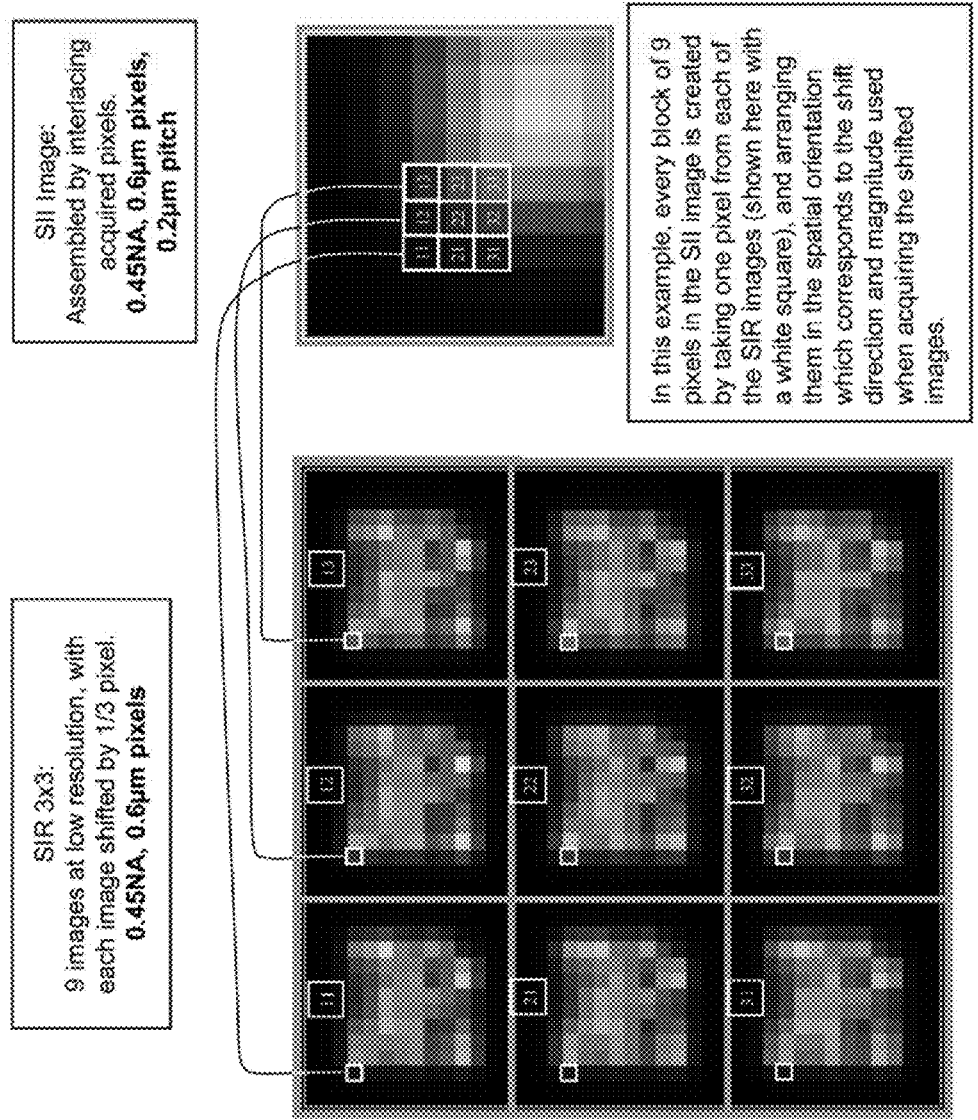
FIGURE 5 – Creation of SII (Simple Image Interlace) Image Pixel Interlace Detail

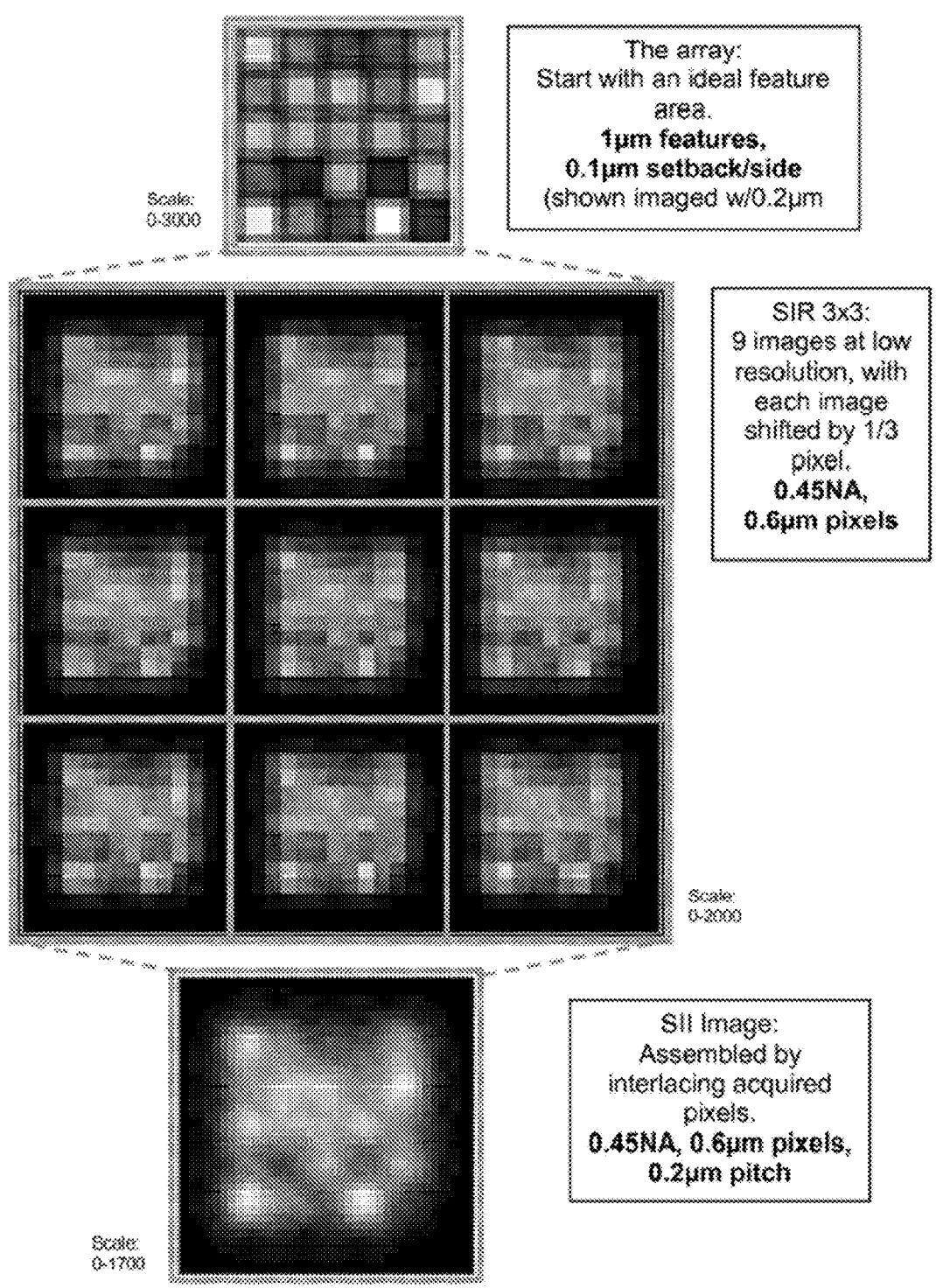

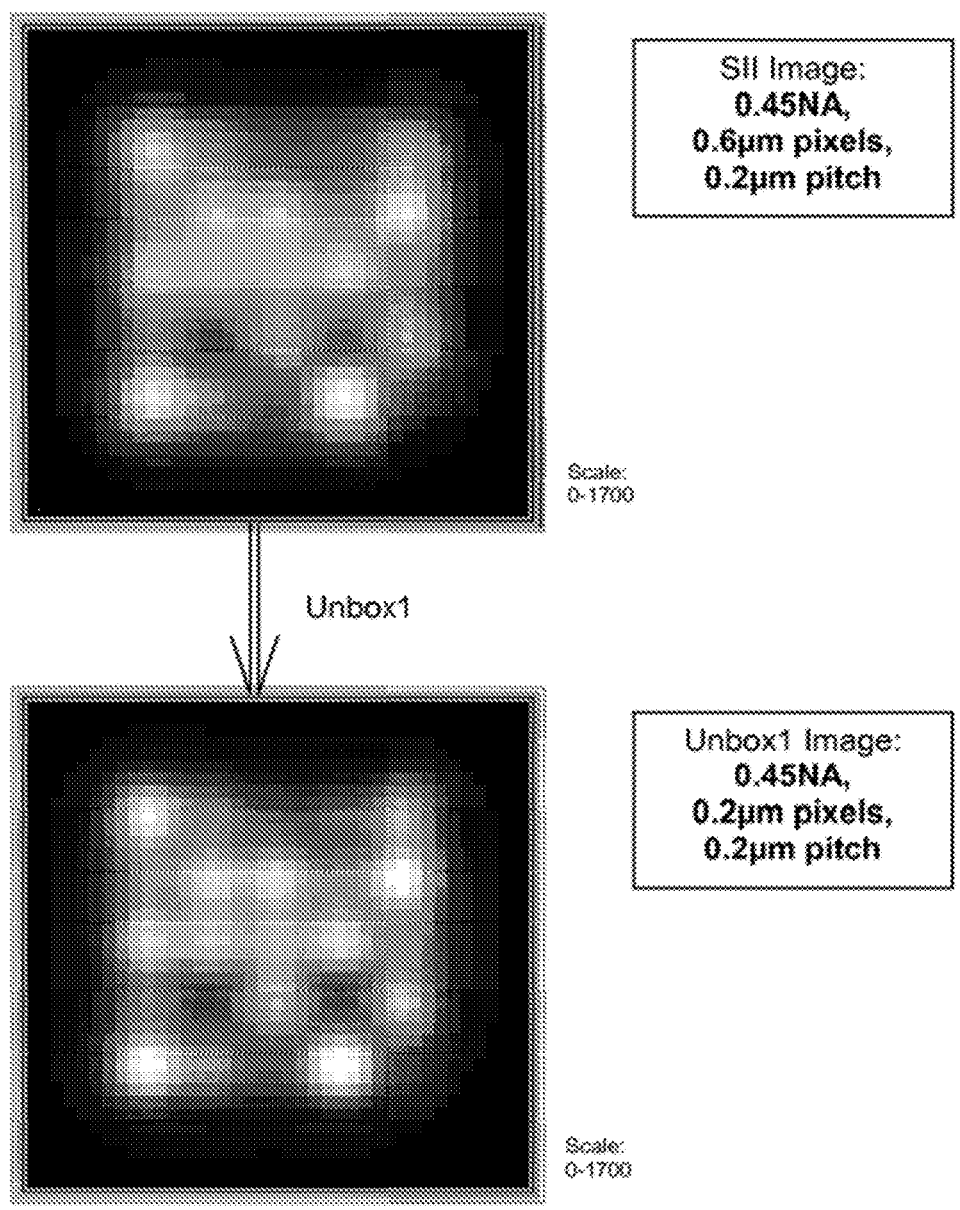

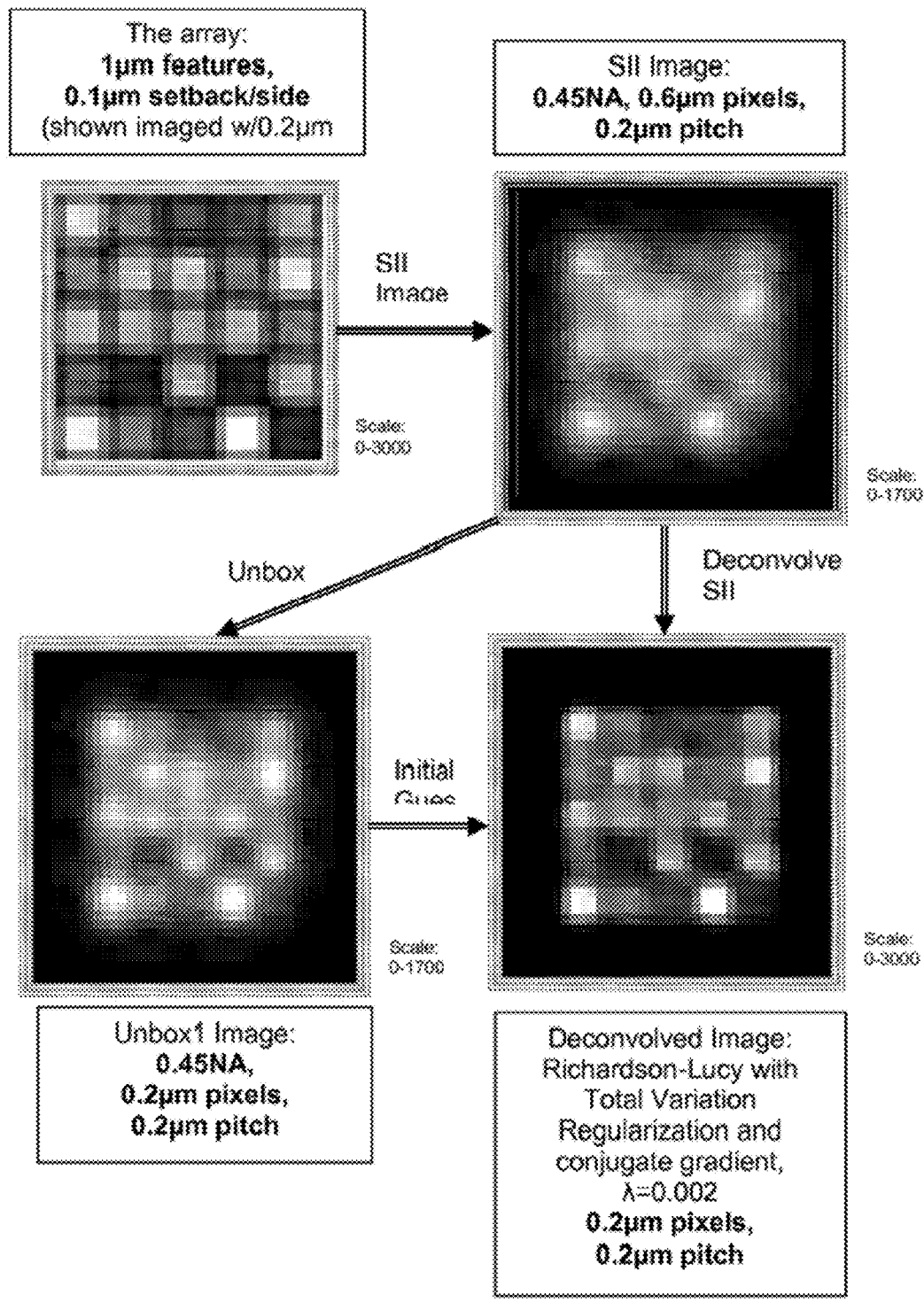

Figure 9 – Unbox Problem, Matrix Notation

The number of rows and columns in the Unboxed image is greater than that in the SII image by Nshifts-1

SII Image:
**SIIRows * SIICols**

Unboxed Image
**SIIRows+Nshifts1 *
SIICols+Nshifts1**

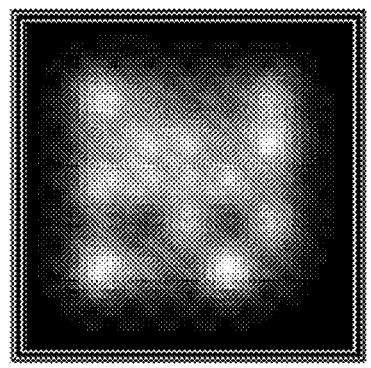

Scale:
0-1700

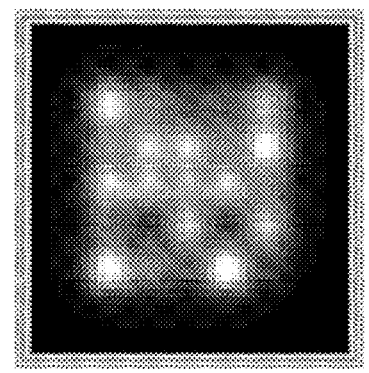

Scale:
0-1700

If we reshape each of these arrays into a column vector (working columnwise), the SII image has dimensions s =(SIIRows * SIICols, 1) and the Unboxed image has dimension u=(SIIRows+Nshifts1 * SIICols+Nshifts1, 1)
The relationship between the Unboxed Image and the SII image can then be expressed in matrix notation:
**A*Uboxc=SIIc**
where Uboxc is the Unboxed Image is column vector form
and SIIc is the SII Image in column vector form.
Since the number of unknowns exceeds the number of independent equations,
this system of equations is underdetermined.

A
SIIRows+Nshifts1 * SIICols+Nshifts1

SIIRows * SIICols

For a 3/3 SIR, each row of the A matrix contains 9 entries of 1/9, corresponding to the elements of the Unboxed Image which make up the corresponding pixel in the SII image

* Uboxc = SIIc

Figure 10 – MatLab Implementation, Algorithm Unbox1

```
function [UnboxedImage] = unbox_image(SIIImage, NShifts)
%
% ************************************************************************
% DESCRIPTION: Unbox an SII image
%
% Using the overlapping information in an SII image, determine the values
% of the pixels which created the SII image.
%
% Algorithm: Solve full system of linear equations, inverse of pixels ->
% SII
% which is slightly underdetermined, using least squares.
%
% This is the simplest algorithm with no additional constraints.
%
% INPUTS:
%     SIIImage: SII (simple image interlace) image
%     NShifts: number of shifts in each axis
%
% RETURNS:
%     UnboxedImage - Unboxed image
% ************************************************************************
%
Diagnostics = false;
if Diagnostics
    SIIImg = SIIImage;         % save copy of SII image
end % reshape the SII image into a column vector
% reshape operates on a column-wise basis
SIIImgSize = size(SIIImage);
SIIRows = SIIImgSize(1); SIICols = SIIImgSize(2);
SIIImage = reshape(SIIImage, SIIRows * SIICols, 1);

% dimensions of Unbox array
UnboxRows = SIIRows + NShifts - 1;
UnboxCols = SIICols + NShifts - 1;

% The "A matrix" is the the matrix to which the Unbox vector is multiplied
% to get the SII column vector.  Each row represents one SII result.  The
% rows produce column-wise results in the SI column vector.
% This is a sparse matrix.
%
% check to see if the "A matrix" exists in a disk file.  If not,
% create it.
AMatrixFilename = sprintf('AMatrix_%u_%u_%u_%u', UnboxRows, UnboxCols,
SIIRows, SIICols);
try
    load(AMatrixFilename);
catch Idx = 1;
    ARow = 1;
    ACols = UnboxRows * UnboxCols;
    ListSize = SIIRows * SIICols * NShifts^2;
    RowList = zeros(1, ListSize);
    ColList = zeros(1, ListSize);
```

Figure 10 (CONTINUED)

```
    % central region, for which there are NShift^2 unbox pixels for every
    % SII pixel
    for r=1:SIIRows
        for c=1:SIICols
            for row=1:NShifts
                for col=1:NShifts
                    ACol = (r+row-2)*UnboxCols + (c+col-1);
                    RowList(Idx) = ARow;
                    ColList(Idx) = ACol;
                    Idx = Idx + 1;
                end
            end
            ARow = ARow + 1;
        end
    end ARows = SIIRows * SIICols;

A = sparse(RowList, ColList, 1, ARows, ACols);

save(AMatrixFilename, 'A');
end

% A * Unbox = SIIImage .* NShifts^2 (SIIImage represented as a column
% vector)
% Use least squares with tolerance of 1e-3 and maximum of 20 iterations.
% These values were imperially determined.  Excess iterations do not
% improve
% the result and cause ringing.
% The direct method of matrix division, in the form of:
%     Unbox = A\SIIImage .* NShifts^2;
% yeilds a mess.
%Unbox = lsqr(A, SIIImage, 1e-3, 20) .* NShifts^2;
[Unbox,flag,relres,iter,resvec] = lsqr(A, SIIImage, 1e-3, 20);
Unbox = Unbox .* NShifts^2;
UnboxedImage = reshape(Unbox, UnboxRows, UnboxCols);

% Diagnostic: Create an SII image from the unboxed image
% See how well it compares to the original SII image
if Diagnostics
    SIIFromUnbox = (A * Unbox) ./ NShifts^2;
    SIIFromUnbox = reshape(SIIFromUnbox, SIIRows, SIICols);
    figure; imagesc(SIIFromUnbox); axis ij; colorbar; ...
        title('SII from Unbox');
    SIIFrUnboxMinusSII = SIIFromUnbox - SIIImg;
    figure;imagesc(SIIFrUnboxMinusSII); axis ij; colorbar; ...
        title('SII minus SII from Unbox');
end
```

**Figure 11 – MatLab Implementation, Algorithm RL
Richardson-Lucy with Total Variation Regularization**

```
function [X,diagnostic] = RL(Y, h, niter, X, lambda, clip, epsilon)
% RL: 2-d Richardson-Lucy Deconvolution
% Required inputs:
%    Y - image to be deconvolved
%    h - point-spread function, with origin in the center
%    niter - number of improvement iterations
% Optional inputs:
%    X - initial guess for result (If omitted or [], default is Y)
%    lambda - controls amount of Total Variation Regularization
%        default=0, means no regularization.
%        Typical values are small, in range 0.001 to 0.03
%    clip - if >0, upper bound to clip estimate before each iteration
%        (default 0)
%    epsilon - zerodivide protective term for TV (default 0.01)
% Outputs:
%    X - deconvolved image
%    diagnostic (optional) - struct of per-iteration diagnostic side
information with fields:
%        .alpha  - the overrelaxation factor applied
%        .alphaMax - the initial limit placed on alpha to avoid negativity
%        .beta   - the CG momentum factor
%        .ll     - log likelihood of obtaining Y given X
%        .rmse   - vector of per-iteration RMS error in reblurred space
%        .time   - cumulative run time to the end of each iteration
% if any(Y(:)<0)
        error('Image to be deconvolved must be nonnegative'), end
    if isinteger(Y), Y=double(Y); end
    if any(h(:)<0), error('Deconvolution kernel must be nonnegative'), end
    if nargin<4 || length(X)==0, X=Y; end
    if nargin<5, lambda=0; end
    if nargin<6, clip=0; end
    if nargin<7, epsilon=0.01; end
    if isinteger(X), X=double(X); end
    if ~(0<=lambda && lambda<=0.1), error('lambda out of bounds'), end tic;
    mn = size(X)+size(h)-1;
    if any(mn<size(Y))
        error('Image too big for initial guess and kernel'), end
    MN = 32*ceil(mn/32);    % Round up to multiple of 32 for faster FT
    M = MN(1); N = MN(2);
    [x1,x2] = size(X);
    [y1,y2] = size(Y);
    [h1,h2] = size(h);

% Expand and circularly shift PSF so its center is at (1,1)
    T = h; T(M,N) = 0;     % T is a reusable temporary
    H = fft2(circshift(T, -floor(size(h)/2)), M, N);
    Hc = conj(H);           % reverse the kernel oldmgll = Inf;          % for early loop termination check
    doCG = false;
    for i=1:niter
```

Figure 11 (CONTINUED)

```
X = max(X, 0.001);                          % Avoid zero divisions
if clip>0
    X = min(X,clip);
end % Find Richardson-Lucy correction factor
if i==1
    T = ifft2(H .* fft2(padWrap(X,M,N)));
    Xh = real(T(1:y1,1:y2));                % X convolved with h
end
YoXh = Y./Xh;
T = ifft2(fft2(padWrap(YoXh,M,N)) .* Hc);
factor = real(T(1:x1,1:x2));                % R-L correction factor % Apply regularization
if lambda>0
    % Total Variation
    factor = factor ./ max((1.0 - lambda.*TV(X,epsilon)), 0.01);

% Tikhonov-Miller
    %laplacian = conv2(X, [1 4 1; 4 -20 4; 1 4 1]/6, 'same');
    %factor = factor ./ max(1 + 3*lambda*laplacian, 0.01);
end % Linearize correction, and find blur of that
dX = X .* (factor-1);                       % Linearized correction term
dXh = real(ifft2(fft2(padWrap(dX,M,N)).*H));
dXh = dXh(1:x1,1:x2);                       % reblurred R-L correction % Conjugate gradient direction adjustment (momentum)
if doCG         % True except 1st iteration or CG restart
    % Polak-Ribiere
    % beta = dXh(:)' * (dXh(:)-dXhold(:)) / (dXhold(:)'*dXhold(:));

% Formula from Hanisch et al.
    T = YoXh .* dXhold ./ Xh;
    beta = - T(:)'*dXh(:) / (T(:)'*dXhold(:));

dX = dX + beta*dXold;
    dXh = dXh + beta*dXhold;
else
    beta = 0;            % for reporting
end
dXold = dX;
dXhold = dXh;

% Overrelaxation acceleration
Xpos = X(:)+0.01;
alphaMax = min(Xpos(:)./max(-dX(:),Xpos/20));
if alphaMax>1
    [alfa,mqll]= fminbnd(@(a) -quasiLogLikelihood(Y, Xh+a*dXh), ...
                  0.5, alphaMax, optimset('TolX', 0.05));
else
    alfa = 1;
    mqll = -quasiLogLikelihood(Y, Xh+dXh);
end
if mqll < oldmqll           % We're improving
```

Figure 11 (CONTINUED)

```
            SuccessfulIterations = i;
            X    = X  + alfa*dX;           Xh = Xh + alfa*dXh;
            oldsqll = sqll;
            doCG = true;
%         elseif doCG          % Worse because regularization, not CG failure
%             fprintf('CG restart ');
%             doCG = false;                % Restart CG
        else
            SuccessfulIterations = i-1;    % Still worse: this triggers exit
            fprintf('break');
        end % Collect diagnostic data
        if nargout>1
            diagnostic.alphaMax(i) = alphaMax;
            diagnostic.alpha(i) = alfa;
            diagnostic.beta(i) = beta;
            diagnostic.ll(i)   = logLikelihood(Y, Xh);
            diagnostic.rmse(i) = rms(Y-Xh);
            %diagnostic.factorLnStd(i) = std(log10(factor(:)));
            diagnostic.time(i) = toc;
            diagnostic.iter = SuccessfulIterations;
        end if SuccessfulIterations ~= i       % early exit
            break;
        end fprintf('%d ', i);
        if mod(i,20) == 0, fprintf('\r'); end
    end
    fprintf('\n');
end % Log likelihood that data image could be result of a Poisson process
% with expected counts equal to the reblur
function lnL = logLikelihood(data, reblur)
    lnL = sum(data(:).*log(reblur(:)) - reblur(:) - gammaln(data(:)+1));
end % Simplified version of logLikelihood that omits the term that doesn't
% vary with the reblurred image
function lnL = quasiLogLikelihood(data, reblur)
    lnL = sum(data(:).*log(reblur(:)) - reblur(:));
end %========================================================================
% Revision: 2.5
%========================================================================
```

Figure 11 (CONTINUED)

```
function divergence = TV(A, epsilon)
% TV: Total variation of a 2-d array
% Inputs:
%    A - the array
%    epsilon - a small term to avoid zero division (default 0.001)
% Returns:
%    Total Variation of A = divergence of del(A) / abs(del(A))
%
% See: Dey et al., "A Deconvolution Method for Confocal Microscopy
% with Total Variation Regularization",
% Proc. IEEE International Symposium on Biomedical Imaging (ISBI), 2004
%
% ------------------------------------------------------------------ if nargin<2, epsilon=0.001; end
    if isinteger(A), A=single(A); end
    [M,N] = size(A);
    nNaN = sum(isnan(A(:)));
    if nNaN>0
        disp(sprintf('TV: %d NaNs', nNaN));
    end b = zeros(M+1,N, class(A));
    b(2:end-1,:) = A(2:end,:) - A(1:end-1,:);
    bs = sign(b);
    ba = abs(b);

c = zeros(M,N+1, class(A));
    c(:,2:end-1) = A(:,2:end) - A(:,1:end-1);
    cs = sign(c);
    ca = abs(c);

g0 = b(2:end,:) ./ sqrt(b(2:end,:).^2 + (0.5*(cs(:,1:end-1)+cs(:,2:end)) .* min(ca(:,1:end-1),ca(:,2:end))).^2 + epsilon.^2);
    g1 = c(:,2:end) ./ sqrt(c(:,2:end).^2 + (0.5*(bs(1:end-1,:)+bs(2:end,:)) .* min(ba(1:end-1,:),ba(2:end,:))).^2 + epsilon.^2);

divergence = zeros(M,N, class(g0));
    divergence(2:end,:) = g0(2:end,:) - g0(1:end-1,:);
    divergence(:,2:end) = divergence(:,2:end) + g1(:,2:end)-g1(:,1:end-1);
end
```

SYSTEM, METHOD, AND PRODUCT FOR IMAGING PROBE ARRAYS WITH SMALL FEATURE SIZES

PRIORITY CLAIM

This application is a continuation of U.S. Non-Provisional patent application Ser. No. 13/241,970, filed Sep. 23, 2011, which is a Continuation of U.S. Non-Provisional patent application Ser. No. 11/627,876, filed Jan. 26, 2007, which claims priority from U.S. Provisional Patent Application No. 60/762,621, filed Jan. 27, 2006, the entire disclosure of which is incorporated herein by reference in its entirety.

BACKGROUND

1. Field of the Invention

The present invention relates to systems and methods for examining biological material. In particular, the invention relates to the analysis of images from scanned biological probe arrays comprising probe features of very small size, such as for instance probe features that are 8 μm or less across. Accurate analysis of small features sizes becomes increasingly more complicated as the feature size becomes smaller where elements of the scanning system may contribute to sources of error in the resulting image. For example, the scanning system may implement a light source focused to a spot and scanned across the probe array where the size of the spot is large in comparison to the size of the probe features and inter-feature spacing on a probe array where the spot size may produce "blurring" in the resulting image. In the present example, the described analysis may preferably be implemented with images generated from a scanning system using a CCD based architecture with a wide field of view which is described in greater detail below.

2. Related Art

Synthesized nucleic acid probe arrays, such as Affymetrix GeneChip® probe arrays, and spotted probe arrays, have been used to generate unprecedented amounts of information about biological systems. For example, the GeneChip® Human Genome U133 Plus 2.0 Array for expression applications available from Affymetrix, Inc. of Santa Clara, Calif., is comprised of one microarray containing 1,300,000 oligonucleotide features covering more than 47,000 transcripts and variants that include 38,500 well characterized human genes. Similarly, the GeneChip® Mapping 500K Array Set for genotyping applications available from Affymetrix, Inc. of Santa Clara, Calif., is comprised of two arrays, each capable of genotyping on average 250,000 SNPs (single nucleotide polymorphism). Analysis of expression or genotyping data from such microarrays may lead to the development of new drugs and new diagnostic tools.

SUMMARY OF THE INVENTION

Systems, methods, and products to address these and other needs are described herein with respect to illustrative, non-limiting, implementation. Various alternatives, modifications and equivalents are possible. For example, certain systems, methods, and computer software products are described herein using exemplary implementations for analyzing data from arrays of biological materials produced by the Affymetrix® 417™ or 427™ Arrayer. Other illustrative implementations are referred to in relation to data from Affymetrix® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may e applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media, which may include polymeric coating or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

An embodiment of a method for resolving features on a probe array is described that, comprises acquiring a plurality of micro-shifted images of a region of a probe array; reconstructing an image of the probe array using the micro-shifted images; and deriving intensity values for one or more probe features disposed on the probe array from the reconstructed image.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment an implementations are illustrative, rather than limiting.

BRIEF DESCRIPTION OF THE DRAWINGS

The above and further features will be more clearly appreciated from the following detailed description when taken in conjunction with the accompanying drawings. In the drawings, life reference numerals indicate like structures or method steps and the leftmost digit of a reference numeral indicates the number of the figure in which the referenced element first appears (for example, the element 150 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

FIG. 3A is a simplified graphical representation of the scanner optics and detectors of FIG. 2, suitable of providing excitation light and the detection of emission signals;

FIG. 3B is a simplified graphical representation of the lens of FIG. 3A enabled to shift one or more lens elements relative to an emission beam; and FIG. 4 is a functional block diagram of one embodiment of the scanner computer of FIG. 2.

FIG. 5 shows a process for creating a SII image.

FIG. 6 shows a process for creating a SII image.

FIG. 7 shows a SII image and the image resulting from running unboxing algorithm, "Unbox1."

FIG. 8 shows how unboxing is used to assist the deconvolution module.

FIG. 9 shows a solution to the Unbox problem using matrix notation.

FIG. 19 shows computer code for a MatLab Implementation using the Algorithm Unbox1.

FIG. 11 shows computer code for the MatLab Implementation using the Algorithm RL Richardson-Lucy with Total Variation Regularization.

DETAILED DESCRIPTION a) General

Figure 1:
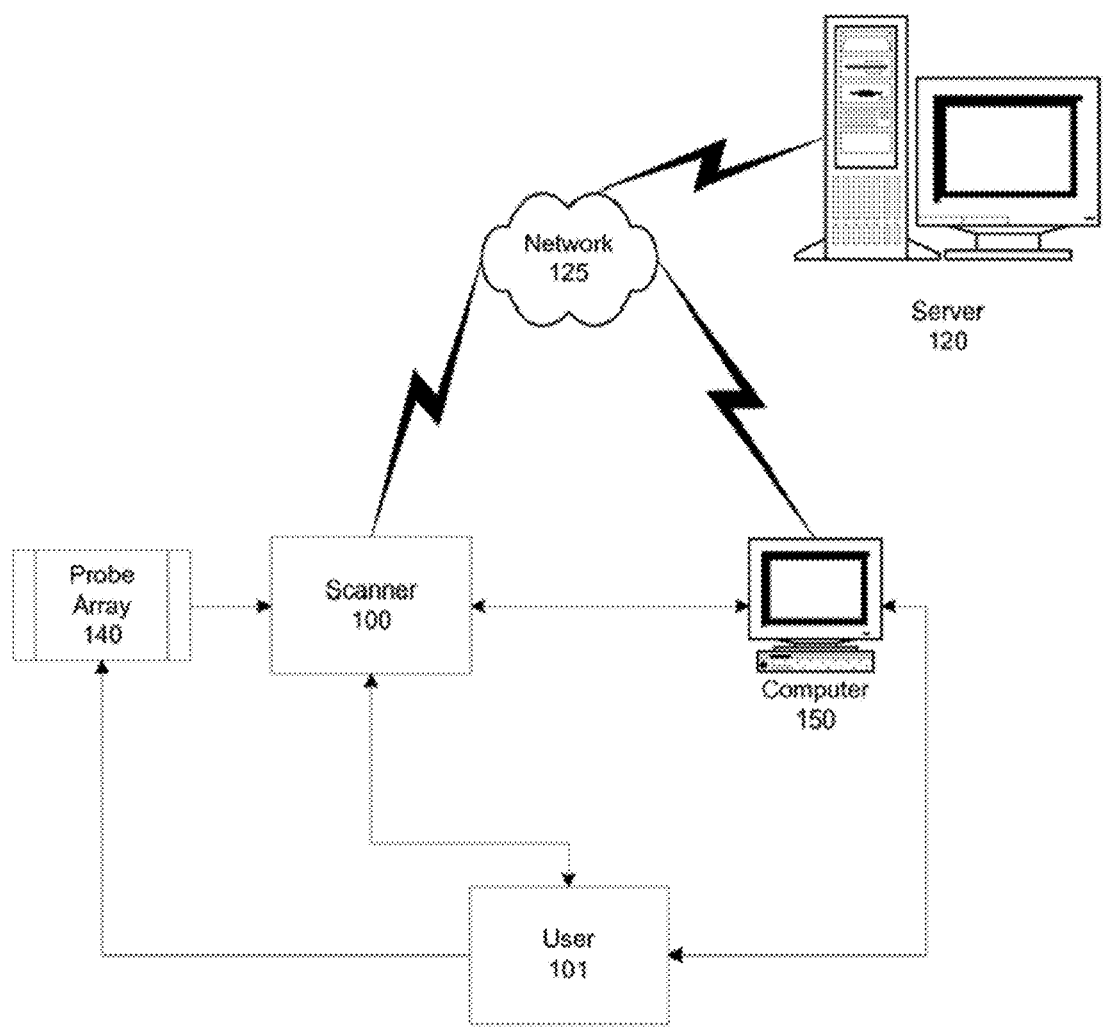
FIG. 1 is a functional block diagram of one embodiment of a scanner instrument enabled to scan a probe array and computer system for image acquisition and analysis.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values with that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are with the skill of the art. Such conventional techniques include polymer array synthesis, hybridization, ligatior, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells; A Laboratory Manual, PCR Primer: A laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841; WO 00/58516; U.S. Pat. Nos. 5,143,854; 5,242,974; 5,252, 743; 5,324,633; 5,384,261; 5,405,783; 5,424,186; 5,451, 683, 5,482,867; 5,491,074; 5,527,681; 5,550,215; 5,571, 639; 5,578,832; 5,593,839; 5,599,695; 5,624,711; 5,631, 734; 5,795,716; 5,831,070; 5,837,832; 5,856,101; 5,858, 659; 5,936,324; 5,968,740; 5,974,164; 5,981,185; 5,981, 956; 6,025,601; 6,033,860; 6,040,193; 6,090,555; 6,136, 269; 6,269,846; and 6,428,752; in PCT Applications Nos. PCT/US99/00730 (International Publication No. WO 99/36760); and PCT/US01/04285 (International Publication No. WO 01/58593); which are all incorporated herein by reference in their entirety for all purposes.

Patents that describe synthesis techniques in specific embodiments include U.S. Pat. Nos. 5,412,087; 6,147,205; 6,262,216; 6,310,189; 5,889,165; and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992; 6,013,440; 6,020,135; 6,033,860; 6,040,138; 6,177,248; and 6,309,822. Genotyping and uses therefore are shown in U.S. Ser. Nos. 10/442,021; 10/013,598 (U.S. Patent Application Publication 20030036069); and U.S. Pat. Nos. 5,856,092; 6,300,063; 5,858,659; 6,284,460; 6,361, 947; 6,368,799; and 6,333,179. Other uses are embodied in U.S. Pat. Nos. 5,871,928; 5,902,723; 6,045,996; 5,541,061; and 6,197,506.

The present invention also contemplates sample preparation methods in certain preferred embodiments. Prior to or concurrent with genotyping, the genomic sample may be amplified by a variety of mechanisms, some of which may employ PCR. See, for example, PCR Technology; Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press. Oxford); and U.S. Pat. Nos. 4,683,262; 4,683,195; 4,800,159; 4,965,188; and 5,333,675, and each of which h incorporated herein by reference in their entireties for all purposes. The sample may be amplified on the array. See, for example, U.S. Pat. No. 6,300,070 and U.S. Ser. No. 09/513, 300, which are incorporated herein by reference.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909; 5,861,245) and nucleic acid based sequence amplification (NABSA). (See, U.S. Pat. Nos. 5,409,818; 5,554,517; and 6,063,603, each of which is incorporated herein by reference). Other amplification methods that may be used are described in, U.S. Pat. Nos. 5,242,794; 5,494,810; 4,988,617; and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. No. 6,361,947, U.S. Pat. No. 6,301,592 and U.S. Ser. Nos. 09/916,135; 09/020,491 (U.S. Patent Application Publication 20030096235); Ser. No. 09/910,292 (U.S. Patent Application Publication 20030082543); and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S. 80: 1194 (1983). Methods and apparatus for carrying out repeated and controlled, hybridization reactions have been described in U.S. Pat. Nos. 5,871,928; 5,874,219; 6,045,996; 6,386,749; and 6,391,623 each of which are incorporated herein by reference.

The present invention also contemplates signal detection of hybridization between ligands in certain preferred embodiments. For example, methods and apparatus for signal detection and processing of intensity data are disclosed in, U.S. Pat. Nos. 5,143,854; 5,547,839; 5,578,832; 5,631,734; 5,800,992; 5,834,758; 5,856,092; 5,902,723; 5,936,324; 5,981,956; 6,025,601; 6,090,555; 6,141,096; 6,171,793; 6,185,030; 6,201,639; 6,207,960; 6,218,803; 6,225,625; 6,252,236; 6,335,824; 6,403,320; 6,407,858; 6,472,671; 6,490,533; 6,650,411; and 6,643,015, in U.S. patent application Ser. Nos. 10/389,194; 60/493,495; and in PCT Application PCT/US99/06007 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed.; 2001). See U.S. Pat. No. 6,420,108.

The present invention may also make use of various computer program products and software for a variety of purposes, such as probe design, management of data, analysis, and instrument operation. See, U.S. Pat. Nos. 5,733,729; 5,593,839; 5,795,716; 5,733,729; 5,974,164; 6,066,454; 6,090,555; 6,185,561; 6,188,783; 6,223,127; 6,228,593; 6,229,911; 6,242,180; 6,308,170; 6,361,937; 6,420,108; 6,484,183; 6,505,125; 6,510,391; 6,532,462; 6,546,340; and 6,687,602.

Additionally, the present invention may have preferred embodiments that include methods for providing genetic information over networks such as the Internet as shown in U.S. Ser. Nos. 10/197,621; 10/063,559 (United States Publication Number 20020183936); 10/065,856; 10/065,808; 10/328,818; 10/328,872; 10/423,403; and 60/482,389.

b) Definitions

The term "admixture" refers to the phenomenon of gene flow between populations resulting from migration. Admixture can create linkage disequilibrium (LD).

The term "allele' as used herein is any one of a number of alternative forms of a given locus (position) on a chromosome. An allele may be used to indicate one form of a polymorphism, for example, a biallelic SNP may have possible alleles A and B. An allele may also be used to indicate a particular combination of alleles of two or more SNPs in a given gene or chromosomal segment. The frequency of an allele in a population is the number of times that specific allele appears divided by the total number of alleles of that locus.

The term "array" as used herein refers to an intentionally created collection of molecules which can be prepared either synthetically or biosynthetically. The molecules in the array can be identical or different from each other. The array can assume a variety of formats, for example, libraries of soluble molecules, libraries of compounds tethered to resin beads, silica chips, or other solid supports.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

The term "biopolymer" or sometimes referred to as "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a biopolymer is a "biomonomer".

The term "combinatorial synthesis strategy" as used herein refers to a combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequences or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with a least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "effective amount" as used herein refers to an amount sufficient to induce a desired result.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotype" as used herein refers to the genetic information an individual carries at one or more positions in the genome. A genotype may refer to the information present at a single polymorphism, for example, a single SNP. For example, if a SNP is biallelic and can be either an A or a C then if an individual is homozygous for A at that position the genotype of the SNP is homozygous A or AA. Genotype may also refer to the information present at a plurality of polymorphic positions.

The term "Hardy-Weinberg equilibrium" (HWE) as used herein refers to the principle that an allele that when homozygous leads to a disorder that prevents the individual from reproducing does not disappear from the population but remains present in a population in the undetectable heterozygous state at a constant allele frequency.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factor may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), LNAs, as described in Koshkin et al. Tetrahedron 54:3607-3630, 1998, and U.S. Pat. No. 6,268,490, aptamers, and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "linkage analysis" as used herein refers to a method of genetic analysis in which data are collected from affected families, and regions of the genome are identified that co-segregated with the disease in many independent families or over many generations of an extended pedigree. A disease locus may be identified because it lies in a region of the genome that is shared by all affected members of a pedigree.

The term "linkage disequilibrium" or sometimes referred to as "allelic association" as used herein refers to the preferential association of a particular allele or genetic marker with a specific allele, or genetic marker at a nearby chromosomal location more frequently than expected by chance for any particular allele frequency in the population. For example, if locus X has alleles A and B, which occur equally frequently, and linked locus Y has alleles C and D, which occur equally frequently, one would expect the combination AC to occur with a frequency of 0.25. If AC occurs more frequently, then alleles A and C are in linkage disequilibrium. Linkage disequilibrium may result from natural selection of certain combination of alleles or because an allele has been introduced into a population too recently to have reached equilibrium with linked alleles. The genetic interval around a disease locus may be narrowed by detecting disequilibrium between nearby markers and the disease locus. For additional information on linkage disequilibrium see Ardlie et al., Nat. Rev. Gen. 3:299309, 2002.

The term "lod score" or "LOD" is the log of the odds ratio of the probability of the data occurring under the specific hypothesis relative to the null hypothesis. LOD=log [probability assuming linkage/probability assuming no linkage].

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, for 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The terms "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Au. The first identified allelic form is arbitrarily designated as the reference from and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies end antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configuration. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as antiprobes. As the term targets is used herein, no difference in meaning is intended. A "Probe Target Pair" is formed when two macromolecules have combined through molecular recognition to form a complex.

c) Embodiments of the Present Invention

Embodiments of an image analysis system are described herein that are enabled to provide reliable data from scanned images of probe arrays comprising small feature sizes. In particular, embodiments are described that are enabled to accurately image and analyze the data associated with features of a probe array that may include feature sizes in a range of 8 µm to 5 µm, 1 µm, or smaller in a dimension (such as the side of a square, side of a rectangle, or diameter of a spot).

Figure 2:
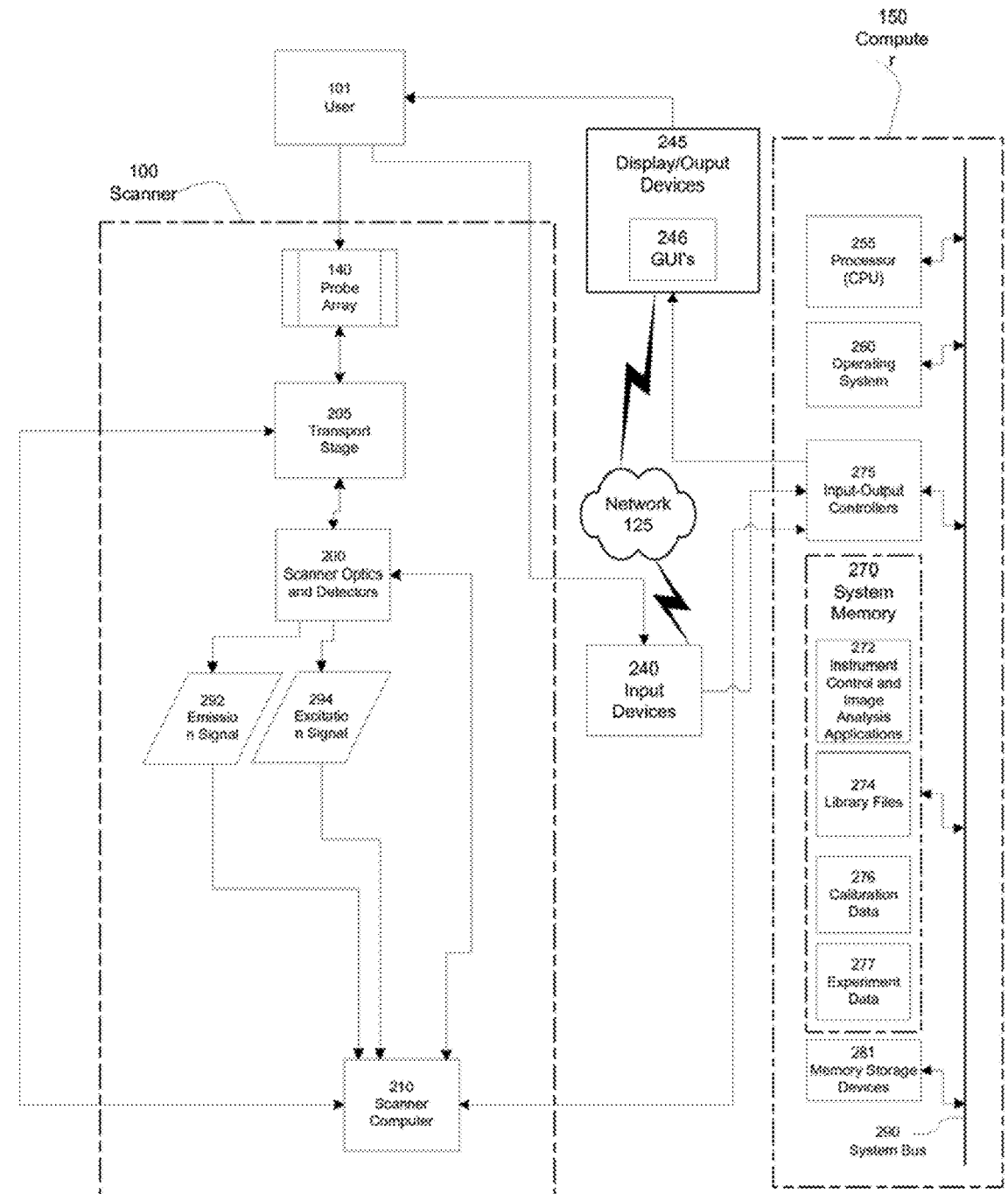
FIG. 2 is a functional block diagram of one embodiment of the scanner-computer system of FIG. 1, including a transport stage, scanner optics and detectors, and a scanner computer comprising instrument control and image analysis applications.

Probe Array 140:

An illustrative example of probe array 140 is provided in FIGS. 1, 2, and 3. Descriptions of probe arrays are provided above with respect to "Nucleic Acid Probe arrays" and other related disclosure. In various implementations, probe array 140 may be disposed in a cartridge or housing such as, for example, the GeneChip® probe array available from Affymetrix, Inc. of Santa Clara Calif. Examples of probe arrays and associated cartridges or housing may be found in U.S. Pat. Nos. 5,945,334, 6,287,850, 6,399,365, 6,551,817, each of which is also hereby incorporated by reference herein in its entirety for all purposes. In addition, some embodiments of probe array 240 may be associated with pegs or posts, where for instance probe array 240 may be affixed via gluing, welding, or other means known in the related art to the peg or post that may be operatively coupled to a tray, strip or other type of similar substrate. Examples with embodiments of probe array 240 associated with pegs or posts may be found in U.S. patent Ser. No. 10/826,577, titled "Immersion Array Plates for Interchangeable Microtiter Well Plates", filed Apr. 16, 2004, which is hereby incorporated by reference herein in its entirety for all purposes.

Server 120:

FIG. 1 shows a typical configuration of a server computer connected to a workstation computer via a network. In some implementations any function ascribed to Server 120 may be carried out by one or more other computers, and/or the functions may be performed in parallel by a group of computers. Network 125 may include a local area network, a wide area network, the Internet, another network, or any combination thereof.

Typically, server 120 is a network-server class of computer designed for servicing a number of workstations or other computer platforms over a network. However, server 120 may be any of a variety of types of general-purpose computers such as a personal computer, workstation, main frame computer or other computer platform now or later developed. Server 120 typically includes known components such as a processor, an operating system, a system memory, memory storage devices, and input-output controllers. It will be understood by those skilled in the relevant art that there are many possible configurations of the components of server 120 that may typically include cache memory, a data backup unit, and many other devices. Similarly, many hardware and associated software or firmware components may be implemented in a network server. For example, components to implement one or more firewalls to protect data and applications, uninterruptible power supplies, LAN switches, web-server routing software, and many other components. Those of ordinary skill in the art will readily appreciate how these and other conventional components may be implemented.

Server 120 may employ one or more processing elements that may, for instance, include multiple processors; e.g., multiple Intel® Core™ 2 Duo 2.66 GHz processors. As further examples, the processing elements may include one or more of a variety of other commercially available processors such as Xeon™, Itanium® 2 64-bit processors or Pentium® processors from Intel, SPARC® processors made by Sun Microsystems, Opteron™ processors from Advanced Micro Devices, or other processors that are or will become available. The processing elements execute the operating system, which may be, for example, a Windows®-type operating system (such as Windows Server System that may include Windows Server 2003, SQL Server® 2005, Windows® 2000 with SP 1, Windows NT®4.0 with SP6a) from the Microsoft Corporation; the Solaris operating system from Sun Microsystems, the Tru64 Unix from Compaq, other Unix® or Linux-type operating systems available from many vendors or open sources; another or a future operating system; or some combination thereof. The operating system interfaces with firmware and hardware in a well-known manner, and facilitates the processor in coordinating and executing the functions of various computer programs that may be written in a variety of programming languages. The operating system, typically in operation with the processor, coordinates and executes functions of the other components of server 120. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, or other memory storage device. The memory storage device may be any of a variety of known or future devices, including a compact disk drives, a tape drive, a removable hard disk drive, flash memory, or a diskette drive. Such types of memory storage device typically read from, and/or write to, a program storage medium (not shown) such as, respectively, a compact disk, magnetic tape, removable hard disk, flash memory, or floppy diskette. Any of these program storage media, or others now is use or that may later be developed, may be considered a computer program product. A will be appreciated, these program storage media typically store a computer software program and/or data. Computer software programs, also called computer control logic, typically are stored in the system memory and/or the program storage device used in conjunction with the memory storage device.

In some embodiments, a computer program product is described comprising a computer usable medium having control logic (computer software program, including program code) stored therein. The control logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

The input-output controllers could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via a system bus. Some of these communications may be accomplished in alternative embodiments using network or other types of remote communications.

As will be evident to those skilled in the relevant art, a server application if implemented in software, may be loaded into the system memory and/or the memory storage device through one of the input devices. All or portions of these loaded elements may also reside in a read-only memory or similar device of the memory storage device, such devices not requiring that the elements first be loaded through the input devices. It will be understood by those skilled in the relevant art that any of the loaded elements, or portions of them, may be loaded by the processor in a known manner into the system memory, or cache memory (not shown), or both, as advantageous for execution.

Scanner 100:

Labeled targets hybridized to probe arrays may be detected using various devices, sometimes referred to as scanners, as described above with respect to methods and apparatus for signal detection. An illustrative device is shown in FIG. 1 as scanner 100, that may incorporate a variety of optical elements such as the example illustrated in FIG. 3 that includes a plurality of optical elements associated with scanner optics and detectors 200. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 µm, 1.5 µm. 1.0 µm, or sub-micron pixel size. Two examples where the signal may be incorporated into data are data files in the form *.dat or *.tif as generated respectively by Affymetrix® Microarray Suite (described in U.S. patent application Ser. No. 10/219,882, which is hereby incorporated by reference herein in its entirety for all purposes) or Affymetrix®GeneChip® Operating Software described in U.S. patent application Ser. No. 10/764,663, which is hereby incorporated by reference herein in its entirety for all purposes) based on images scanned from GeneChip® arrays, and Affymetrix® Jaguar™ software (described in U.S. patent application Ser. No. 09/682,071, which is hereby incorporated by reference herein in its entirety for all purposes) based on images scanned from spotted arrays. Examples of scanner systems that may be implemented with embodiments of the present invention include U.S. patent application Ser. Nos. 10/389,194; and 10/846,261, both of which are incorporated by reference above; and U.S. patent application Ser. No. 10/846,261, titled "System, Method, and Product for Providing A Wavelength-Tunable Excitation Beam", filed May 13, 2004, and U.S. patent application Ser. No. 11/260,617, titled "System, Method and Product for Multiple Wavelength Detection Using Single Source Excitation", filed Oct. 27, 2005, each of which is hereby incorporated by reference herein in its entirety for all purposes.

Embodiments of the presently described invention may bed employed with images generated by implementations of an image acquisition device, such as a scanner 100, comprising various optical architectures, but may be preferably employed with images generated using an implementation of scanner 100 comprising a sensing element, such as a CD based optical architecture with what may be referred to as a wide field of view. For example, a CCD based architecture may employ some or all of the components described with respect to scanner optics and detectors 200, but typically may not need particular components such as, for instance, implementations of a pinhole in beam 352, or embodiments of detector 390 that includes a photomultiplier tube which may be more amenable to a confocal or other similar type of optical architecture.

Computer 150:

An illustrative example of computer 150 is provided in FIG. 1 and also in greater detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input devices 240, and display/output devices 245. Display/Output Devices 245 may include display devices that provides visual information, this information typically may be logically and/or physically organized as an array of pixels. A Graphical user interface (GUI) controller may also be included that may comprise any of a variety of known or future software programs for providing graphical input and output interfaces such as for instance GUI's 246. For example, GUI's 246 may provide one or more graphical representations to a user, such as user 101, and also be enabled to process user inputs via GUI's 246 using means of selection or input known to those of ordinary skill in the related art.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor such as a Core™ 2 Duo, Itanium® or Pentium® processor made by Intel Corporation, a SPARC® processor made by Sun Microsystems, an Athlon™ or Opteron™ processor made by AMD corporation, or it may be one of other processors that are or will become available. Processor 255 executes operating system 260, which may be, for example, a Windows®-type operating system (such as Windows NT® 4.0 with SP6a, or Windows XP) from the Microsoft Corporation; a Unix® or Linux-type operating system available from many vendors or what is referred to as an open source; another or a future operating system; or some combination thereof. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk driver, flash memory, or a diskette drive. Such types of memory storage devices 281 typically read from, and/or write to, a program storage medium (not shown) such as, respectively, a compact disk, magnetic tape, removable hard disk, flash memory, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

As will be evident to those skilled in the relevant art, instrument control and image processing applications 272, if implemented in software, may be loaded into and executed from system memory 270 and/or memory storage device 281. All or portions of applications 272 may also reside in a read-only memory or similar device of memory storage device 281, such devices not requiring that applications 272 first be loaded through input-output controllers 275. It will be understood by those skilled in the relevant art that applications 272, or portions of it, may be loaded by processor 255 in a known manner into system memory 270, or cache memory (not shown), or both, as advantageous for execution. Also illustrated in FIG. 2 are library files 274, calibration data 276, and experiment data 277 stored in system memory 270. For example, calibration data 276 could include one or more values or other types of calibration data related to the calibration of scanner 100 or other instrument. Additionally, experiment data 277 could include data related to one or more experiments or assays such as excitation wavelength ranges, emission wavelength ranges, extinction coefficients and/or associated excitation power level values, or other values associated with one or more fluorescent labels.

Network 125 may included one or more of the many various types of networks well known to those of ordinary skill in the art. For example, network 125 may include what is commonly referred to as a TCP/IP network, or other type of network that may include the internet, or intranet architectures.

Scanner Optics and Detectors 200:

FIG. 3 provides a simplified graphical example of possible embodiments of optical elements associated with scanner 100, illustrated as scanner optics and detectors 200.

Elements of optics and detectors 200 may include one or more sources 320, such as source 320A and source 320B that could comprise Light emitting Diodes (sometimes referred to as LED's), or other type of light source known in the art. Typically, source 320 provides light within the excitation range of one or more fluorescent labels associated with target molecules hybridized to probes disposed on probe array 140 or fluorescent labels associated with a calibration standard. For instance, some embodiments of LED's provide sufficient levels of power to evoke fluorescent emissions from fluorophores. A single LED of this type may be employed as a source to provide excitation light to probe array 140. The term "power" in this context refers to the capability to evoke emissions. For example, the power of an excitation beam generally refers to photon number or energy per unit of time and typically may be measured in milliwatts of light energy with respect to the present example in which the light energy evokes a fluorescent signal.

LED's of this type provide advantages in certain embodiments over other types of sources due to their low cost, high output efficiency, long life, short on/off-off/on transition time, large selection of wavelengths, and low heat production. For example, an embodiment of source 320 may comprise an LED that could include a "Luxeon™ III" light-emitting diode manufactured by Lumileds Lighting LLC (San Jose Calif., model LXHL-LE3C or LXHL-LM3C). In the present example, source 320A may be employed to provide light within a range of one or more excitation wavelengths that could, for instance, include a nominal central wavelength of 505 nm or 530 nm. Also, source 320B may be employed to provide light having a nominal central wavelength of 590 nm.

Some embodiments of source 320 may be driven by one or more elements associated with scanner 200 or more particularly by one or more elements of scanner computer 210, computer 150, or other elements that may be employed in the art. For example, each of sources 320A and 320A may be driven in what may be referred to as constant-current mode. Devices capable of providing constant-current mode include a Texas Instruments model PT6214 regulator. In the present example, the PT6214 regulator may be configured as a current source by means of a current-sensing feedback resistor in order to provide the desired functionality. In the same or alternative implementations what may be referred to as a LM317 regulator could be employed instead of a PT6214 or combinations of the two could be employed where each regulator implementation may provide different desirable characteristics associated with the implementation of source 320.

Continuing with the above example, each regulator or element may preferably set the current delivered to source 320A and/or 320B. In the present example, a current of 0.9 A may be employed that equates to a value that is 90 percent of the maximum recommended current for implementations of source 320, resulting in the production of heat that may include a measure of approximately 3 W of heat output. Typically, each implementation of source 320 is mounted on a finned heat sink, or other type of heat dissipation element known in the art that could also optionally include one or more active cooling elements such as for instance a fan. Additionally, the current delivered to source 320A and/or 320B may be turned on ad off using one or more elements that could for instance employ what may be referred to as a TTL signal. The one or more elements could include one or more auxiliary outputs of a motion controller associated with scanner computer 210 or computer 150. In the same or alternative examples, the TTL signal may be buffered by what may be referred to as a SN7407 or similar open-collector buffer. Also, the one or more elements may apply the TTL signal to one or more elements of the regulator such as what may be referred to as an "Inhibit" pin of the regulator.

Some embodiments of source 320 could also comprise a laser such as, for instance, a solid state, diode pumped, frequency doubled Nd:YAG (Neodymium-doped Yttrium Aluminum Garnet) or YVO4 laser producing green laser light, having a wavelength of 532 nm or other laser implementation. Also, those of ordinary skill in the related art will appreciate that other types of sources 320 may be employed in the present invention such as incandescent sources, halogen or xenon sources, metal halide sources, mercury vapor sources, or other sources known in the art.

In some embodiments, source 320A and/or 320B may be employed to provide beam 335 and/or beam 337 comprising excitation light to probe array 140. In the example provided in FIG. 3 beam 335 may pass through one or more optical elements to condition or promote desirable characteristics of beam 335. For example, lens 323 may be employed to "collimate" beam 335. The term "collimate" as used herein generally refers to a beam of light where the rays are parallel to one another generating a parallel beam. Typically, a collimated beam provides what those of ordinary skill in the related art refer to as a plane wavefront characteristic of beam 335 or 337. For example, in some implementations the positional relationship of lens 323 with an embodiment of source 320 is important to produce the desired optical characteristics. In particular, for lens 323 to effectively collimate light it should be placed at a distance equal to the focal length of lens 323 from source 320. In the present example, lens 323 may include an aspheric lens having a focal length of 17 mm and a diameter of 25 mm (Newport Corp, Irvine Calif., model KPA031-C).

Some preferred embodiments of the present invention include source 320A providing excitation light for one or more fluorescent labels as previously described and source 320B providing a range of one or more wavelengths of light useful for other purposes such as for automatic focusing operations. In the presently described embodiments beam 339 may include beam 335, beam 337 or a combination of both.

In the example provided in FIG. 3, after collimation by lens 323 beam 335 may travel through aperture 325 that may shape beam 335. For example, aperture 325 may include a thin black-anodized aluminum disk containing an 11 mm×8.5 mm rectangular opening. In the present example, aperture 325 may be employed to match the illuminated area of probe array 140 to the field of view of detector 390. Typically, illuminating an unnecessarily large area is undesirable because it increases the amount of stray light reaching detector 390 and because most fluorescent labels are susceptible to photobleaching. However, in some embodiments aperture 325 can optionally be omitted. In the example where aperture 325 is omitted, the distance from lens 323 to lens 329 is equal to the focal length of lens 329, and an image of the pupil of lens 323 is formed at probe array 140. The sample is uniformly illuminated if the pupil of lens 323 is uniformly filled by light from source 320A. This optical arrangement is generally referred to by those of ordinary skill in the related art as Kohler illumination.

Next, embodiments of beam 335 may travel to filter 327. Filter 327 may be used to remove or block light at wavelengths other than excitation wavelengths, and generally need not be included if, for example, source 320A does not produce light at these extraneous wavelengths. However, it may be desirable in some applications to use inexpensive sources and often it is cheaper to filter out-of-mode light than to design the source to avoid producing such extraneous emissions. In some embodiments, filter 327 allows all or a substantial portion of light at one or more excitation wavelengths to pass through without affecting other characteristics of beam 335, such as the desirable characteristics modified by lens 323. Also, a plurality of filters 327 may also be associated with a filter wheel or other means for selectively translating a desired filter in the optical path. For example, some embodiments of filter 327 may include a 470-550 nm bandpass filter manufactured by Chroma Technology Corp (Rockingham Vt., model HQ510/80) or a 550-nm shortpass filter.

In some embodiments of scanner optics and detectors 200, one or more components may be placed in the optical path of beam 335 or 337 after elements such as filter 327 to selectively manipulate the direction of travel. One such element may include beam splitter 340. Those of ordinary skill in the related art will appreciate that beam splitter 340 may include a dichroic beam splitter, also commonly referred to as a dichroic mirror. Those of ordinary skill in the related art will appreciate that beam splitter 340 may include an optical element that is highly reflective to light of a certain wavelength range, and allow transmission of light through the beam splitter or mirror at one or more other wavelength ranges. In some embodiments, beam splitter 340 could also include what is referred to as a geometric beam splitter where a portion of the surface of beam splitter 340 is reflective to all light or light within a particular range of wavelengths, and the remaining portion is permissive to the light. Also, some embodiments of beam splitter 340 may reflect a certain percentage of light at a particular wavelength and allow transmission of the remaining percentage. For example, beam splitter 340 may reflect substantially all wavelengths of light associated with beam 335 and transmit substantially all wavelengths of light associated with beam 337. Also in the present example, beam splitter 340' may reflect substantially all wavelengths of light associated with beam 339 that may comprise the wavelengths associated with both beam 335 and 337, and transmit substantially all wavelengths of light associated with beam 352 from probe array 140. In the present example, beam splitter 340 could include a longpass dichroic beam splitter having high reflectance at 470-550 nm and high transmittance at 570-610 nm. One specific type may be referred to as a "cold mirror" with a reflectance of at least 90% across the visible spectrum (Melles Griot, Carlsbad Calif., model 03 MCS 007).

As described above, FIG. 3 illustrates beam 339 exiting beam splitter 340 that may be representative of beam 335, beam 337, or both. In some embodiments lens 329 may be employed to focus beam 339 at aperture 343 associated with lens 350, where for example, the distance from lens 329 to aperture 343 may be equal to the focal length of lens 329. In the present example lens 329 includes a plan-convex lens having a focal length of 150 mm (Edmund Industrial Optics, Barrington N.J., model 32-975) that forms an image of source 320A at aperture 343, where the size of this image is equal to the diameter of beam 335 output by source 320A multiplied by the focal length of lens 329 and divided by the focal length of lens 323. In some embodiments lens 350 may comprise a telecentric lens, where the distance from aperture 343 to lens 350 is equal to the focal length of lens 350. In alternative embodiments where lens 350 is not telecentric, the distance from aperture 343 to lens 350 may be zero.

Typically, lens 350 will focus beam 339 at probe array 140. In some embodiments, lens 150 may include a small lightweight lens, and a preferred embodiment is a diffraction limited optical element. For example, when detector 390 comprises a CCD type architecture it may typically be desirable for lens 350 to have what may be referred to as a wide field of view that may for instance comprise characteristics such as what those of ordinary skill in the related art may refer to as an Airy point spread function (given perfect optics). Those of ordinary skill in the related art will appreciate that what may be referred to as the "Point Spread Function" (hereafter referred to as PSF) provides a measure of "blurring" from a single point object introduced into an image from an optical system such as for instance scanner 100. In the present example, the PSF may be described by a mathematical function that describes the optical distortion of the point source through the optical path of an instrument and may differ between instruments, as well as differing between image acquisition events in the same instrument. Also, an optical detection instrument such as scanner 100 may comprise different PSFs for different focal and/or spatial locations and further the PSF may not be a linear function.

Some embodiments of lens 350 may include what is referred to as a 20× infinite-conjugate microscope objective having a numerical aperture of 0.45 and a focal length of 10 mm (Nikon Inc, Melville N.Y., model CFI Plan Fluor ELWD 20xC, MRH08220). Other embodiments comprising similar microscope objectives are available from other manufacturers, but may differ in focal length. Also, lens 350 may be optimized to reduce what is referred to a spherical aberration that could be caused by factors such as a thick cover glass or alternatively lens 370 may be enabled to perform this function. Some embodiments of lens 350 (such as the Nikon MRH08220) may contain an adjustment to compensate for a range of cover glass thicknesses.

As described above, lens 350 focuses beam 339 at a region of probe array 140. In response, one or more fluorophore labels associated with the biological materials emit emission beam 352 at characteristic wavelengths in accordance with well-known principles. The term "fluorophore" commonly refers to a molecule which will absorb energy of a specific wavelength and re-emit energy at a different wavelength. For example, types of fluorophore species that may typically be employed in conjunction with probe array 140 may include one or more of R-phycoerytherin, fluorescein, CY3, CY5, rhodamine, lanthanide-chelate fluorophores, one or more species of Semiconductor nanocrystals (commonly referred to as Quantum Dots available from Quantum Dot Corp, Hayward Calif., or Evident Technologies, Troy N.Y.), what may be referred to as FRET (referred to as Fluorescence Resonant Energy Transfer) type species, or other types of fluorophore commonly employed in the art. Those of ordinary skill in the related art will appreciate that FRET may be achieved when there re two fluorophore species present in the same molecule. The emission wavelength of one fluorophore overlaps the excitation wavelength of the second fluorophore and results in the emission of a wavelength from the second fluorophore that is atypical of the class of fluorophores that use that excitation wavelength. Also, quantum dots are tunable such that multiple quantum dot species may be employed so that each specie excites at a particular wavelength but has a different characteristic emission spectrum. Thus by using an excitation beam of a single wavelength it is possible to obtain distinctly different emissions so that different features of a probe array could be labeled in a single experiment.

Light emitted, reflected, or back-scattered by probe array 140 is represented as beam 352 and in some embodiments is collimated by lens 350. Beam 352 in the illustrated example follows the reverse optical path as described with respect to beam 339 until reaching beam splitter 340'. In accordance with well known techniques and principles, the characteristics of beam splitter 340' are selected so that substantially all of beam 352 (or a portion of it) passes through the beam splitter 340' rather than being reflected. Emission beam 352 is then directed along a desired optical path to filter 360.

Filter 360 may comprise some or all of the characteristics as described above with respect to filter 327. In some embodiments, filter 360 may be provided to filter out spectral components of emission beam 352 that are outside of the mission spectra of one or more particular fluorophore species. The term "emission spectra" generally refers to one or more characteristic emission wavelengths or range of wavelengths of those fluorophore species that are responsive to beam 339. Embodiments of filter 360 may include a 570-610 nm bandpass filter (Chroma Technology Corp, model HQ590/40) or a 570-nm longpass filter.

In some implementations filter 360 is capable of holding a plurality of filters that each could be tuned to different wavelengths corresponding to the emission spectra from different fluorophore species. For example, filter 360 may include what is referred to as a filter wheel that may include a mechanism for turning the wheel to position a desired filter in the optical path of emission beam 352. The mechanism may include a motor or some other device for turning or translation that may be responsive to instructions from application 272 and/or firmware 472. For example, beam 339 from source 320A may comprise one or more wavelengths that may include a range of wavelengths that excite one or more fluorophore species where the amount of energy absorbed and re-emitted by each fluorophore species in its emission spectrum is a function of its extinction coefficient and the power level of beam 339. In the present example, the filter wheel of filter 360 may be translated with respect to the optical path of emission beam 352 to position a filter that is complementary to the emission spectrum of the particular fluorophore species in order to remove light components from emission beam 352 that are outside of the emission spectrum. The source of the undesirable light components could include undesirable fluorescence generated by other fluorophore species, emissions from glass, glue, or other components associated with elements such as supports, substrates, or housings for probe array 140, or other sources known to those of ordinary skill in the related art.

Beam 352 may also, in some embodiments pass through lens 370 to promote desirable characteristics. Some of these characteristics may for example include, but are not limited to, promoting a preferred effective pixel size and a field of view. For example, some embodiments may include an effective pixel size of 0.20 µm and a field of view of 15.155 mm×15.155 mm. In the present example, lens 370 may be constructed from one or more lens elements such as one achromatic cemented doublet (Linos, model G322246), having a focal length of 180 mm and a diameter of 40 mm. When using more than one lens element, the focal lengths of each element that comprises lens 370 do not need to be equal. Alternatively, lens 370 can be a camera lens, or a custom multi-element lens.

Some embodiments of lens 370 may be enabled to "shift" position of the lens elements in one or more of the X and Y axes relative to the plane of the substrate associated with probe array 140. Shifting the lens elements of lens 370 by some dimension results in a shift of beam 352 by some dimension relative to the detector elements of detector 390. FIG. 3B provides a simplified, illustrative example of one possible embodiment for means to shift one or more lens elements. Lens 370 may comprise housing 372 that in some embodiments may provide a stationary anchor for the translation of shift element 375. In the present example shift element 375 may comprise a low, fixed mass operatively coupled to one or more lens elements 377 where there may be fixed positional relationship between shift element 375 and the one or more lens elements 377. Thus, translating shift element in one or more of the X or Y axes by some dimension results in a shift of the one or more lens elements 377 relative to the input of beam 352. In some embodiments each of lens elements 377 may be corrected for spherical aberration so that a shift of shift element 375 results in a consistent and predictable shift of the point of focus relative to the detector elements of detector 390. In the present example, shift elements may be translated using a translation means that may comprise one or more piezoelectric motors, micro-stepped motor/drivers, open loop drive mechanism or other type of motorized mechanism. The translation means may be operated under the control of applications 272 or 472, or one or more motions controllers commonly employed in the art.

After passing through lens 370, beam 352 continues along a desired optical path and impinges upon detector 390. In some embodiments, detector 390 may be a silicon detector for providing an electrical signal representative of detected light, or it may be a photodiode, a charge-coupled device (i.e. CCD), a CID, a photomultiplier tube, or any other detection device that is now available or that may be developed in the future for providing a signal indicative of detected light. Detector 390 generates signal 292 that may in some embodiments comprise values associated with photon counts or other measure of intensity that represents beam 352. For example detector 390 may include a CCD sensor (Kodak KAI-4010M) and a camera (Roper Scientific, Inc., model K4). In the present example, detector 390 may include certain characteristics including but not limited to an array of 2048×2048 pixels, each pixel comprising a dimension of 7.4 microns square, and what is referred to as dark current of approximately 0.1 electron/pixel/second when the CCD sensor is cooled to −25° C. Further detector 390 may include what is referred to as a "cooled camera," accomplishing cooling utilizing a thermoelectric cooling element or other ordinary means. In some situations, and "uncooled camera" may be utilized. Some embodiments of detector 390 may also employ similar CCD type cameras available from other manufacturers such as Hamamatsu Corp. (Bridgewater, N.H.), Photometrics (Tucson Ariz.), Cooke Corp (Romulus Mich.), Sensovation (Belmont Calif.), and Apogee Instruments Inc (Auburn Calif.).

Some embodiments of scanner optics and detectors 200 may comprise one or more elements not illustrated in FIG. 3, such as for instance one or more turning mirrors. Turning mirrors are commonly associated with optical systems to provide the necessary adjustments to what may be referred to as the optical path such as, for instance, to allow for alignment of beam 339 at lens 350 and to allow for alignment of beam 352 at detector 390. For example, turning mirrors serve to "fold" the optical path into a more compact size & shape to facilitate overall scanner packaging. The number of turning mirrors may vary in different embodiments and may depend on the requirements of the optical path.

An additional example of a scanner system with a similar optical architecture is described in U.S. Provisional Patent Application Ser. No. 60/673,969, titled "Methods and Devices for Reading Microarray", filed Apr. 22, 2005, which is hereby incorporated by reference herein in its entirety for all purposes.

Transport Stage 205:

Another element of scanner 100 may, in some embodiments, include transport stage 205 that provides all of the degrees of freedom required to manipulate probe array 140 for the purposes of auto-focus, scanning, and calibration operations. Those of ordinary skill in the related art will appreciate that the term "degrees of freedom" generally refers to the number of independent parameters required to specify the position and orientation of an object. For example, in one embodiment, probe array 140 may be surrounded or encased by a housing that for instance would include a cartridge with a clear window for optical access to probe array 140. In the present example the cartridge could include one or more features such as a tab or keyed element that interfaces with transport stage 205 and defines the positional relationship of frame 205 and the cartridge. Alternatively, embodiments of probe array 140 may be disposed upon a peg or post type of structure that is operatively coupled to a substrate such as a tray or strip, where the embodiments of probe array 140 is spaced apart from the substrate by a distance that is equal to the height of the peg or post. Frame 205 may then manipulate the position of the cartridge or peg/post substrate relative to one or mom elements of scanner 100 such as, for instance, lens 350.

In one embodiment transport stage 205 is capable of manipulating probe array 140 in six possible degrees of freedom such as, for example, what may be generally referred to as yaw, roll, pitch, Z, X and Y. Probe array 140 may be brought into best focus by adjusting the distance between probe array 140 and lens 350. In some implementations, the distance adjustment may be employed by moving the position of one or more elements of transport stage 205, such as a focus stage, in the Z axis. For example, movement of the focus stage in the Z axis may be actuated by one or more motors in a first direction that may decrease the distance between probe array 140 and lens 345, as well as the opposite direction that may increase the distance.

Translation of probe array 140 along the X, and Y axes (X and Y axes may typically be in a plane that is substantially parallel to the plane of the substrate of probe array 140) may in one embodiment be accomplished by a precision linear stage, coupled to what is referred to as one or more piezo-electric motors, micro-stepped motor/drivers, open loop drive mechanism or other type of motorized mechanism. The linear stage may include one or more guide elements to support and guide the described embodiments of probe array 140 and additional elements to secure said embodiments during scanner operation. In some implementations, the linear stage may include independent position adjustment mechanisms enabled to adjust the position of probe array 140 in a plurality of axes such that adjustment in one axis is less likely to affect the adjustments in other axes.

In some implementations, the housing or substrate associated with probe array 140 generally remains in the same plane of orientation with respect to scanner 100 from the point that it is loaded into scanner 100 to the point at which it is ejected. This may apply to all operations of the scanner including the auto-focus and scan operations.

An example of a transport stage sometimes referred to as translation stage may include a 3-axis translation stage available from Delton Precision Inc, Bethel Conn., model LS2-1-A05-XYZ-E-NPN-I.

Additional examples of transport stages and means for manipulating the position of a probe array for the purposes of scanning are described in U.S. patent application Ser. No. 10/380,194, incorporated by reference above.

Scanner Computer 210:

As illustrated in FIG. 4, scanner computer 210 may include elements such as processor 455, operating system 460, input-output controllers 475, system memory 470, memory storage devices 481, and system bus 490 that may, in some implementations, have the same characteristics of corresponding elements in computer 150. Other elements of scanner computer 210 may include scanner firmware 472, scanner parameter data 477, and service application 478 that will each be described in detail below.

Scanner firmware 472 may, in many implementations, be enabled to control all functions of scanner 100 based, at least in part, upon data stored locally in scanner parameter data 477 or remotely in one or more data files from one or more remote sources. For example, the remote data source could include computer 150 that includes library files 274, calibration data 276, and experiment data 277 stored in system memory 270. In the present example, the flow of data to scanner computer 210 may be managed by instrument control and image analysis applications 272 that may be responsive to data requests from firmware 472.

A possible advantage of including scanner computer 210 in a particular implementation is that scanner 100 may be network based and/or otherwise arranged so that a user computer, such as computer 150, is not required. Input-output controllers 475 may include what is commonly referred to by those of ordinary skill in the related art as a TCP/IP network connection. The term "TCP/IP" generally refers to a set of protocols that enable the connection of a number of different networks into a network of networks (i.e. the Internet). Scanner computer 210 may use the network connection to connect to one or more computers, such as computer 150, in place of a traditional configuration that includes a "hardwire" connection between a scanner instrument and a single computer. For example, the network connection of input-output controllers 475 may allow for scanner 100 and one more computers to be located remotely from one another. Additionally, a plurality of users, each with their own computer, may utilize scanner 100 independently. In some implementations it is desirable that only a single computer is allowed to connect to scanner 100 at a time. Alternative, a single may interact with a plurality of scanners. In the present example, all calibration and instrument specific information may be stored in one or more locations in scanner computer 210 that may be made available to the one or more computers as they interface with scanner computer 210.

The network based implementation of scanner 100 described above may include methods that enable scanner 100 to operate unimpaired during adverse situations that, for instance, may include network disconnects, heavy network loading, electrical interference with the network connection, or other types of adverse event. In some implementations, scanner 100 may require a periodic signal from computer 150 to indicate that the connection is intact. If scanner 100 does not receive that signal within an expected period of time, scanner 100 may operate on the assumption that the network connection has been lost and start storing data that would have been transmitted. When the network connection has been reacquired to scanner 100, all collected data and related information may be transferred to computer 150 that would have normally been transferred if the network connection remained intact. For example, during the occurrence of an adverse situation scanner 100 may lose the network connection to computer 150. The methods enable scanner 100 to operate normally including the acquisition of image data and other operations without interruption. Scanner 100 may store the acquired image data of at least one complete scanned image in memory storage devices 418 to insure that the data is not lost.

In some embodiments, scanner computer 210 may also enable scanner 100 to be configured as a standalone instrument that does not depend upon a controlling workstation. Scanner computer 210 may acquire and store image data as well as function as a data server to multiple clients for efficient data transfer. For example, memory storage devices 480 may include a hard disk or other type of mass storage medium that may be enabled to hold large volumes of image, calibration, and scanner parameter data. Scanner 100 may additionally include a barcode tender, RFID detector, Magnetic strip detector, or other type of device that reads one or more identifiers from one or more labels or tags associated with probe array 140. Scanner computer 210 may execute tire scan operations based, at least in part, upon one or more data files associated with the identifiers, and store the acquired image data on the hard disk. Additionally, scanner 100 may provide a network file system or FTP service enabling one or more remote computers to query and upload scanned images as well as providing an interface enabling the computer to query scanner data and statistics.

It will be understood by those of ordinary skill in the related art that the operations of scanner computer 210 may be performed by a variety of other servers or computers, such as for instance computer 150, a server such as a GCOS server, or that computer 210 may not necessarily reside in scanner 100.

Instrument Control and Image Processing Applications 272:

Instrument control and image processing applications 272 may be any of a variety of known or future image processing applications. Examples of applications 272 include Affymetrix® Microarray Suite, Affymetrix® GeneChip® Operating Software (hereafter referred to as GCOS), and Affymetrix®Jaguar™ software, noted above. Applications 272 may be loaded into system memory 270 and/or memory storage device 281 through one of input devices 240.

Embodiments of applications 272 include executable code being stored in system memory 270 of an implementation of computer 150. Applications 272 may provide a user interface for both the client workstation and one or more servers 120 such as, for instance, GeneChip® Operating Software Server (GCOS Server) available from Affymetrix, Inc. Santa Clara, Calif. Applications 272 could additionally provide the user interface for one or more other workstations and/or one or more instruments. In the presently described implementation, the interface may communicate with and control one or more elements of the one or more servers, one or more workstations, and the one or more instruments. In the described implementation the client workstation could be located locally or remotely to the one or more servers and/or one or more other workstations, and/or one or more instruments. The user interface may, in the present implementation, include an interactive graphical user interface (generally referred to as a GUI), such as GUI's 246, that allow a user to make selections based upon information presented in the GUI. For example, applications 272 may provide a GUI 246 that allows a user to select from a variety of options including data selection, experiment parameters, calibration values, probe array information. Applications 272 may also provide a graphical representation of raw or processed image data where the processed image data may also include annotation information superimposed upon the image such as, for instance, base calls, feature of the probe array, or other useful annotation information. Further examples of providing annotation information on image data are provided in U.S. Provisional Patent Application Ser. No. 60/493,950, titled "System, Method, and Product for Displaying Annotation Information Associated with Microarray Image Data", filed Aug. 8, 2003, which is hereby incorporated by reference herein in its entirety for all purposes.

In alternative implementations, applications 272 may be executed on a server, or on one or more other computer platforms connected directly or indirectly (e.g., via another network, including the Internet or an Intranet) to network 125.

Embodiments of applications 272 also include instrument control features. The instrument control features may include the control of one or more elements of one or more instruments that could, for instance, include elements of a fluid processing station, what may be referred to as an automatic cartridge or tray loader, one or more robotic elements, and scanner 100. The instrument control features may also be capable of receiving information from the one more instruments that could include experiment or instrument status, process steps, or other relevant information. The instrument control features could, for example, be under the control of or an element of the user interface. In the present example, a user may input desired control commands and/or receive the instrument control information via one of GUI's 246. Additional examples of instrument control via a GUI or other interface is provided in U.S. Provisional patent application Ser. No. 10/764,663, titled "System, Method and Computer Software Product for Instrument Control, Data Acquisition, Analysis, Management and Storage", filed Jan. 26, 2004, which is hereby incorporated by reference herein in its entirety for all purposes.

In some embodiments, image data is operated upon by applications 272 to generate intermediate results. Examples of intermediate results include so-called cell intensity files (*.cel) and chip files (*.chp) generated by Affymetrix® GeneChip® Operating Software or Affymetrix® Microarray Suite (as described, for example, in U.S. patent application Ser. Nos. 10/219,882, and 10/764,663, both of which are hereby incorporated herein by reference in their entireties for all purposes) and spot files (*.spt) generated by Affymetrix® Jaguar™ software (as described, for example, in PCT Application PCT/US 01/26390; in U.S. Pat. Nos. 6,829,376, 6,789,040, and 6,965,704; and U.S. patent application Ser. No. 09/682,071, all of which are hereby incorporated by reference herein in their entireties for all purposes). For convenience, the term "file" often is used herein to refer to data generated or used by applications 272 and executable counterparts of other applications, but any of a variety of alternative techniques known in the relevant art for storing, conveying, and/or manipulating data may be employed.

For example, applications 272 receives image data derived from a GeneChip® probe array and generates a cell intensity file. This file contains, for each probe scanned by scanner 100, a single value representative of the intensities of pixels measured by scanner 100 for that probe. Thus, this value is a measure of the abundance of tagged mRNA's present in the target that hybridized to the corresponding probe. Many such mRNA's may be present in each probe, as a probe on a GeneChip® probe array may include, for example, millions of oligonucleotides designed to detect the mRNA's. As noted, another file illustratively assumed to be generated by applications 272 is a chip file. In the present example, in which applications 272 include Affymetrix® GeneChip® Operating Software, the chip file is derived from analysis of the *.cel file combined in some cases with information derived from lab data and/or library files 274 that specify details regarding the sequences and locations of probes and controls. The resulting data stored in the chip file includes degrees of hybridization, absolute and/or differential (over two or more experiments) expression, genotype comparisons, detection of polymorphisms and mutations, and other analytical results.

In another example, in which applications 272 includes Affymetrix® Jaguar™ software operating on image data from a spotted probe array, the resulting spot file includes the intensities of labeled targets that hybridized to probes in the array. Further details regarding cell files, chip files, and spot files are provided in U.S. Pat. No. 6,789,040 incorporated by reference above, as well as U.S. patent application Ser. Nos. 10/126,468; and 09/682,098; which are hereby incorporated by reference herein in their entireties for all purposes. As will be appreciated by those skilled in the relevant art, the preceding and following descriptions of files generated by applications 272 are exemplary only, and the data described, and other data, may be processed, combined, arranged, and/or presented in many other ways.

User 101 and/or automated data input devices or programs (not shown) may provide data related to the design or conduct of experiments. As one further non-limiting example related to the processing of an Affymetrix GeneChip® probe array, the user may specify an Affymetrix catalogue or custom chip type (e.g., Human Genome U133 plus 2.0 chip) either by selecting from a predetermined list presented by GCOS or by scanning a bar code, Radio Frequency Identification (RFID), or other means of electronic identification related to a chip to read its type. GCOS may associate the chip type with various scanning parameters stored in data tables including the area of the chip that is to be scanned, the location of chrome borders or elements on the array used for auto-focusing, the wavelength or intensity/power of excitation light to be used in reading the chip, and so on. As noted, applications 272 may apply some of this data in the generation of intermediate results. For example, information about the dyes may be incorporated into determinations of relative expression.

Those of ordinary skill in the related art will appreciate that one or more operations of applications 272 may be performed by software or firmware associated with various instruments. For example, scanner 100 could include a computer that may include a firmware component that performs or controls one or more operations associated with scanner 100, such as for instance scanner computer 210 and scanner firmware 472.

Some embodiments of applications 272 may be enabled to analyze data produced by scanning implementations of probe array 140 that comprise small feature sizes relative to one or more elements or characteristics of scanner 100 or probe array 140. For example, some embodiments of probe array 140 may comprise 1, 6, 10, 20, 30 or 40 million, or more probe features, where each probe feature occupies an area of the substrate of probe array 140 that, as those of ordinary skill will appreciate, becomes increasingly small as the density of probe features on probe array 140 increases. Embodiments of probe array 140 may comprise probe features that are square, rectangular, octagonal, hexagonal, round, or other shape where each probe feature may also be separated from each other by a boundary region where there are no probe sequences disposed upon the substrate and in some embodiments may be useful to provide an indicative level of the amount of background signal (i.e. signal not generated by emission from the hybridizes probes) in the acquired image. As previously stated, each probe feature may range in size including 8 µm, 5 µm, 1 µm, or smaller in a dimension (such as the side of a square, side of a rectangle, dimension at the widest point, or diameter of a spot), and each boundary region between probe features may be similarly small including a 1 µm, 0.5 µm 0.2 µm, 0.1 µm or smaller boundary.

As the probe features of probe array 140 become increasingly small with respect to elements or characteristics of the system, such as scanner 100 and/or applications 272, it may be come increasingly difficult to acquire and analyze the data produced in order to make reliable determinations of hybridization events associated with one or more of the probe features. For example, scanner 100 includes source 320A and 320B that, as described above, may include a laser, wide spectrum bulb, LED, or other source, that produces excitation light that is focused by lens 350. The dimension of an area illuminate don probe array 140 may vary as described above, and in certain embodiments may be dependent upon one or more characteristics of optics and detectors 200 such as for instance characteristics of lens 350.

For example, some embodiments of applications 272 may analyze and "reconstruct" the data from a plurality of raw images of probe array 140 in order to accurately identify and register probe features in the field of view. Those of ordinary skill in the related art will appreciate that properly registered features enables accurate extraction of intensity information associated with each probe feature.

Some conventional embodiments of a scanner comprising CCD type detection image each probe feature on probe array 140 with an M×N array of CCD pixels. The use of an array of multiple pixels for each probe feature enables an image analysis application to locate the probe feature on the array, separate it from adjacent probe features, and properly determine the amplitude of signal detected from the probe feature. For example, implementations of probe array 140 may compose a plurality of probe features 8 µm in dimension (the dimension may include the side of a square, side of a rectangle, dimension at the widest point, or diameter of a spot, etc. as described above), where an array of 8×8, 1 µm pixels may be employed to image each probe feature. Therefore, if a CCD detector comprises an array of 1000× 1000 pixels, and an objective lens to make each pixel map to a 1 µm area on probe array 140, then the scanner will have a field of view of an area of about 1 mm×1 mm comprising an array of 125×125 probe features. For embodiments of probe array 140 comprising an active area dimension of 6.5 mm×6.5 mm the scanner will have to image 49 (an array of 7×7 separate image acquisitions) sub-arrays to account for all of the probe features represented on the probe array. In addition, for each image acquisition step the scanner and instrument control application will need to perform a move of either probe array 140 or the objective lens to position the sub-array in the field of view and perform a focus operation. In the present example, the process of acquiring images of 49 sub-arrays may be performed within a reasonable period of time for most users.

Continuing to example from above, if the same methods are applied to an embodiment of probe array 140 comprising a 1 µm probe feature dimension the result is much different where the number of sub-array images becomes quite large. For instance, if the same array of 8×8 pixels is employed as described above for each 1 µm probe feature, the magnification of the objective lens would have to be increased by a factor of eight. The resulting field of view would then be 0.125×0.125 mm. Therefore, if the embodiment of probe array 140 comprises an active area dimension of 6.5 mm×6.5 mm as described above, the scanner will have to image 2704 (52×52) sub-array images. Those of ordinary skill in the related art will appreciate that acquiring 2704 images each with a repositioning and focusing step would require a period of time that most users would be unwilling to endure. In addition, such a period of time would likely seriously compromise the biological integrity of probe array 140 and seriously diminish the quality of the resulting data.

The utility of the presently described invention includes systems, methods, and computer software for efficiently scanning probe arrays comprising small probe feature dimensions and analyzing the resulting images to accurately resolve the individual probe features for extraction of intensity information from each feature. As described above, it is desirable for users to be able to scan embodiments of probe array 140 comprising 1 µm probe features in a reasonable amount of time while preserving the ability to accurately resolve the probe features from the resulting images and derive meaningful results. Those of ordinary skill in the related art will appreciate that embodiments of probe array 140 with 1 µm probe features comprise a significantly greater number of probe features in comparison to arrays with 8 µm probe features and thus have substantially greater content providing the user with much richer data.

Embodiments are not described with respect to what may be referred to as "Shifted Image Reconstruction". Certain embodiments may employ optical elements enabling system resolution of less than or equal to 1 pixel per probe feature. For example, detector 390 may include a CCD array detector that typically comprise an array of detection elements that may be calibrated through the use of optical components to look at (i.e. focus on) areas or regions of a specific size, such as a 1 µm square region of the array where the probe features may be positioned on a 1 µm pitch (probe feature ~0.8 µm with ~0.2 µm total setback [which is the space between features]). In the present example, a CCD detector may include a 2048×2048 array of elements each focused to a 0.6 µm region where the regions are contiguously arranged. Therefore, when an image is acquired it will include 4,194, 304 data points of contiguous 0.6 µm regions on the array corresponding to the 1 µm probe feature pitch.

Typically, each pixel is not perfectly registered with each probe feature when focused at probe array 140. In other words the positional relationship between areas that define the boundaries of the pixels focused at probe array 140 and the areas defined by the probe features is unknown. Also, those of ordinary skill in the related art will appreciate that a detected intensity value associated with each pixel is representative of all light collected for, the region that the pixel is focused on. So, if a probe feature overlaps the boundary between two pixels then each pixel will include a measure of intensity contributed from the probe feature that is proportional to the are of the probe feature within the boundary of each pixel. Therefore, assigning proportional intensity from array features to pixels is important.

In order to accurately resolve the 1 µm probe features using the 0.6 µm pixels, Applications 272 acquires a series of micro-shifted images associated with each sub-array area and reconstructs the resolved image from the series of micro-shifted images. For example, Applications 272 employs a means to shift each image in the X and Y axes relative to the plane of the substrate of probe array 140 where the X and Y axes are substantially parallel to the plane of the substrate. In the present example, the micro-shifts comprise increments smaller than one-half the size of the smallest array feature that satisfy particular optical sampling functions such as what may be referred to as the Nyquist sampling criterion. In addition, the number of micro-shifted images acquired by applications 272 may include a number calculated as NX×NY images. Where NX equals the (X size of the CCD pixel)/(the increment step size), and NY equals the (Y size of the CCD pixel)/(the increment step size).

There are a number of methods and elements that can be employed to achieve the micro-shifts necessary for each acquisition. One such method may include translating transport stage 205 operatively coupled to probe array 140 in nanometer increments in the X and Y axes. For example, transport stage 205 may comprise a combination of a nano-shift stage coupled to a gross-motion stage. The nano-shift stage may be particularly adapted to accurately providing translation in nanometer increments that the gross-motion stage may not be capable of. Also, the gross-motion stage may be particularly adapted to providing translation in much greater increments such as for translation between the area defined by the sub-array images that the nano-shift stage may not be suitable for.

Another means and method comprises an implementation that does not require the movement of either probe array 140 or lens 350. One advantage of maintaining the positional relationship between probe array 140 and lens 350 is that it eliminates the need to re-focus after each micro-shift. Another advantage of the presently described method is that the degree of dimension of the shift required is dependent of the size of the CCD pixel rather than the image pixel size. Typically, the CCD pixel size may for instance be 7.4 µm in dimension that is substantially larger than the image pixel size that may be 0.6 µm. Therefore, since the degree of micro-shift is a function of pixel size (i.e. either the CCD pixel or image pixel since both are associated and proportional) then the shift in CCD pixel size requires a less precise shift. In other words, the shift for a CCD pixel may be measured in µm and a shift in image pixel may be measured in nm. For example, applications 272 may translate shift element 375 of lens 370 in the X and/or Y axes relative to the positions of lens 350 and detector 390, where the degree of shift may include a value that is $1/3^{rd}$ the size of a 7.4 µm CCD pixel that is equal to a 2.47 µm distance. Shift element 375, which houses and moves the lens element 377, moves in increments of (1/N)*PixelSize, where N is any integer greater than or equal to 2, preferred integers are 2, 3, 4, 5, 6, 7, 8, 9 and single integers that are higher. The result is a lateral image shift with minimal aberration that is proportional to the degree and direction of shift of beam 352 on the detector elements of detector 390.

Yet another means and method of micro-shift translation comprises shifting the CCD array within detector 390 relative to beam 352. For example, typical CCD arrays have very low mass and therefore shift and settle very quickly. The CCD may be shifted the same amount as the shift element 375 above.

Also, application 272 and/or 472 may synchronize each micro-shift with the CCD clear and expose processes, thereby achieving the maximum possible throughput for a given exposure time.

After acquisition of the micro-shifted images, application 274 reconstructs a resoled image using the information from the micro-shifted images. In some implementations applications 272 may also use values, models, or other type of algorithmic solution for one or more characteristics of the optical system. For example, one such characteristic may include the Point Spread Function (PSF) that may be important to solve some reconstruction solutions. Applications 272 may employ one or more methods associated with image acquisition and/or system calibration to accurately measure the PSF associated with scanner 100 and in some cases employing a certain set of imaging parameters. Typically, applications will need to image one or more point sources to calculate the PSF which may include one or more features associated with a calibration element on probe array 140.

Applications may empty one or more techniques of methods to reconstruct an image from the plurality of micro-shifted images. For example, applications 272 may employ what is referred to as a "Simple Image Interlace" (SII) technique that simply combines a pixel from the same position in each of the micro-shifted images and places them in a region of the reconstructed image, tiled per the spatial layout of the micro-shifted images (having the most overlap with the preceding image). The process is repeated for each of the pixel positions associated with the micro-shifted images. The process of creating an SII image from a set of 3×3 SIR shifted images is shown in FIGS. 5 and 6. FIG. 6 shows a synthetic array (start image), containing 5×5 features on 1 µm pitch, with 0.1 µm setback per side (active feature area 8.8 µm$^2$, with 0.2 µm between features). This start image is then imaged by an optical system with 0.45 NA and a pixel size of 0.64 µm. A total of nine images, in a 3×3 array, are taken, each shifted by $1/3$ pixel (3 horizontal shifts and 3 vertical shifts). The pixels from these shifted images are then tiled together to form the SII image. From FIG. 6, it is clear that any one of the nine SIR shifted images is a poor representation of the start image. However, combined to form an SII image, they form the basis for a reasonable reconstruction of the start image. FIG. 5 contains a detail of how a single pixel, taken from the same location in each of the nine SIR shifted images are combined to form a 3×3 pixel group within the SII image. The arrangement of pixels corresponds to the shift direction and magnitude used when acquiring the images.

Another method applied by Applicators 272 may employ what is sometimes referred to as an unboxing method. In an SII image, the resulting pixels are not mathematically independent. For example, in a 3×3 SIR, each SII pixel is made up of nine subpixels. In the SII image, adjacent horizontal pixels contain six common subpixels. Adjacent vertical pixels contain six common subpixels, as well. This commonality, or overlap, provides the basis for a system of linear equations which can be solved to determine the values of the underlying subpixels. It is the simultaneous solution to this set of equations which provides the resolution enhancement, which is a critical aspect of this invention. In the system previously described, with a pixel size of 0.6 μm and 3×3 shifts, the solution of the unboxing problem yields a subpixel resolution of 2.02 μm. FIG. 7 shows a SII image and the image resulting from running unboxing algorithm, "Unbox1." The improvement in image clarity is quite evident. Both the SII image and the Unbox1 image have pixels on 0.2 μm pitch. The pixels in the SII image, however, represent the average of 3×3 subpixel area, in effect, a low pass filter. The Unbox1 image is sharper in that the low pass effect is removed.

The SII image is equivalent to the results of imaging with a hypothetical camera with pixels arrayed on fine-pitch centers (equal to the actual pixel pitch divided by the interleave factor), but with oversized, overlapping pixels equal in size to those of the actual camera. It is also equivalent to recording the image with a camera containing fine pitch, nonoverlapping pixels, followed by smoothing (convolving) the image with a square, flat box filter.

The "unboxing" of the image undoes the effects of blurring due to the overlapping sensor pixels, but there remains a blurring due to the wave nature of light. The function which characterized how an ideal spot of light gets spread out on the focal plane is called the point spread function, or PSF. Mathematically, we say that the ideal lineage is convolved with the PSF to form the burred image on the focal plane. So the SII image results from convolving the ideal image successively with the optical PSF and then with the box PSF (and adding noise). A procedure called deconvolution can preferably be applied to reverse these two blurring processes insofar as possible.

We may choose to deconvolve the unboxed image with the optical PSF to obtain our recovered image. Alternatively, we may choose to convolve the optical PSF with the box PSF to form a composite PSF, against which we deconvolve the SII image directly. If we choose an iterative-improvement deconvolution algorithm such as Richardson-Lucy, the latter course is preferred, because it checks consistency with the original image data at each step. (For the Richardson-Lucy algorithm, see the following references which are hereby incorporated by reference in their entireties: Journal of the Optical Society of America, Volume 62, Number 1, January 1972, "Bayesian-Based Iterative Method of Image Restoration," William Hadley Richardson, The Astronomical Journal, Volume 79, Number 6, June 1974, "An iterative technique for the rectification of observed distributions," L. B. Lucy). Nevertheless, such an algorithm works better both in the quality of results and in execution time, if it has a good provisional solution with which to start. The unboxing algorithm is useful in providing a good initial solution. FIG. 8 shows how unboxing is used to assist the deconvolution module.

To those skilled in the art of linear algebra, it is clear that the solution to the set of linear equations required to unbox an image is underdetermined (the number of variables exceeds the number of independent equations). Therefore, many solutions will exist which satisfy this set of equations, not all of which will be meaningful. It is imperative that the solution method use as much a-priori knowledge as possible to arrive at the solution which most likely represents the actual subpixel values which created the SII image. When starting a solution, it is useful to linearize the 2-dimensional matrices to set up the problem as a classical matrix problem in the form of: Ax=b. FIG. 9 describes this. If an SII Image contains (SIIRows, SIICols), the corresponding UnboxImage (given Nshifts SIR shifts) will contain (SIIRows+Nshifts-1, SIICols+Nshifts-1). In order to utilize the Ax=b matrix form, each of these matrices need to be converted (columnwise) to a column vector.

Unboxed Image→Uboxc(SIIRows+Nshifts-1*SIICols+Nshifts-1,1).

SII Image→SIIc(SIIRows*SIICols,1).

The relationship between them can now be written as: A*Uboxc=SIIc, where A is a matrix with (SIIRows*SIICols) rows and (SIIRows+Nshifts-1*SIICols+Nshifts-1) columns. Each row of A contains Nshift instances of 1/Nshift, corresponding to the pixels in Uboxc which make up the corresponding pixel in SIIc. There are many methods available to solve for Uboxc. The simplest is least squares minimization. A MatLab implementation of this is shown in FIG. 10. (MatLab is a piece of commercial software, available from The MathWorks, Natick, Mass.). Better solutions may be obtained using methods such as, constrained least squares, iterative constrained least squares and optimization of poisson log-likelihood. Additional use of a priori knowledge, such as feature size, location, or geometry may further improve the solution.

A number of algorithms are available for deconvolution. The simplest and fastest are the linear operations such as Wiener deconvolution and Constrained Least Squares restoration (Digital Image Processing, Kenneth Castleman, 1996 Prentice-Hall, p. 390-396). These methods emphasize the high spatial frequencies in the image which are rolled off by the optical and SH convolutions. But they produce oscillations in the result image, and can produce negative pixel values which represent nonphysical solutions. Many iterative deconvolution algorithms exhibit the same drawbacks, but the Richardson-Lucy algorithm is rooted in the physics of photon arrival at the focal plane, and never produces nonphysical negative results.

Another method applied by applications 272 may employ what can be referred to as the SIR3 method. For example, SIR3 may employ similar concepts to what is known in the art as "Algebraic Reconstruction Technique" (ART) that is employed in the art if tomographic imaging. Also, some implementations may perform updates in parallel instead of sequential updates with part of a pixel's "neighborhood" update and are similar to techniques referred to as "Simultaneous AFT" (SART). For example ART, SART, and SIR-3 may employ additive updates that refer to the difference between the re-blurred solution image and the original image spread back to the solution according to the PSF. In some embodiments, better results may be obtained by changing to multiplicative updates, using the ratio by which the original image mismatches the original, (still spreading back by the PSF), resembles what is referred to as the Richardson-Lucy algorithm.

The Richardson-Lucy algorithm proceeds as follows. Suppose, the point spread function, or PSF, is a characterization of how light spreads, or is scattered, during imaging. This process is called convolution, and it blurs the image. What we want to do is to undo the blurring which is called deconvolution. For example, there is a true image T, and a blurred image B (which also contains some noise). Ignoring noise, we write B=K*T which means B is kernel K convolved with true image T ("*" is convolution). We want to recover an estimate of T. Call this deconvolved image D (the initial guess or estimate). Iterative forms of deconvolution improve the estimate D with each cycle through the following sequence of steps: 1.) R=K*D, R is the reblurred image we get by convolving K with D. 2.) Compare R with B (pixel by pixel). If D is a good estimate of T, then R will be a good match for B. For Richardson-Lucy, the correction term is C=B/R (pixel by pixel division of captured and reblurred images). 3.) Use the correction term C between R and B to inform us how to correct D. For Richardson-Lucy, this is D(new)=D(old)×C*Kr, where x means pixel-by-pixel multiplication, * is convolution, and Kr is the reversal of kernel K. Reversal is flipping the kernel both left-right and up-down. This is equivalent to rotating it 180 degrees. In our example, K is symmetric, so Kr=K. This cycle is repeated as needed until the difference between R and B become small.

The initial guess (D) could be an image wherein all pixels are the same (e.g., 1.0). For Richardson-Lucy, it is required that the total intensity in the pixel is greater than zero. Additionally, D could equal B for the first guess. (But if any pixel of B is zero, use a small positive number like 1.0 instead.) Alternatively, the initial guess could also be the outcome of a 1-step linear deconvolution such as the Wiener or Constrained Least Squares methods. A preferred embodiment is to let D equal the result of unboxing. The use of Unboxing may result in fewer iterations, which saves computation time and means less sensitivity to noise.

In some embodiments, especially those, such as the Affymetrix GeneChip® array, which contain features of uniform size, on a uniform grid, the Richardson-Lucy algorithm may be improved by use of Total Variation Regularization (Institut National De Recherche En Informatique Et En Automatique, "3D Microscopy Deconvolution using Richardson-Lucy Algorithm with Total Variation Regularization," Nicolas Dey, Laure Blanc-F'Eraud, Christophe Zimmer, Pascal Roux, Zvi Kam, Jean-Christophe Olivo-Marin, Josiane Zerubia).

Richardson-Lucy with Total Variation Regularization (RLTV) can be additionally controlled by three independent parameters which must be set to optimize performance. They are alpha: over-relaxation, or acceleration, beta: momentum, and lambda: total variation control. The RLTV algorithm may be optimized by automatically adjusting and optimizing the value of the alpha parameter on each algorithm iteration, along the lines described by Holmes and Liu (Journal of the Optical Society of America, Volume 8, Number 6, June 1991, "Acceleration of maximum-likelihood image restoration for fluorescence microscopy and other noncoherent imagery," Timothy J. Holmes and Yi-Hwa Liu. Furthermore, the value of the beta parameter can be optimized on a per-iteration basis, utilizing a conjugate gradient method similar to that described by Shewchuk (School of Computer Science, Carnegie Mellon University, Aug. 4, 1994, "An Introduction to the Conjugate Gradient Method Without the Agonizing Pain," Jonathan Richard Shewchuk). An implementation of an RLTV algorithm with automatic adjustment of the alpha and beta parameters on a per-iteration basis is shown in FIG. 11. In this implementation, the only remaining input parameter is lambda, which relates to the desired degree of Total Variation Regularization).

Other methods for resolving small feature sizes are described in U.S. patent application Ser. No. 11,289,975, titled "System, Method, and Product for Analyzing Images Comprising Small Feature Sizes", filed Nov. 30, 2005, which is hereby incorporated by reference herein in its entirety for all purposes.

Some embodiments of applications may receive one or more parameters for image acquisition and/or processing from user 101 via one or more GUI's 246. Similarly, applications 272 may provide user 101 one or more micro-shifted images, reconstructed images, or other types of associated data. Applications may also store the aforementioned images or data in one or more databases or as data files. Additional examples of instrument control and image processing applications are described in U.S. patent application Ser. No. 60/669,526, titled "System, Methods and Computer Product for Simplified Instrument Control and File Management", filed Apr. 8, 2005, which is hereby incorporated by reference herein in its entirety for all purposes.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so one may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of riles may be used and various described data structures of files may be combined or otherwise arranged. Numerous other embodiments, and modifications thereof, are contemplated as falling within the scope of the present invention as defined by appended claims and equivalents thereto.

What is claimed is:

1. A method for resolving features on a probe array, comprising:
   acquiring a set of micro-shifted images of a region of a probe array comprising features, wherein the images are acquired using an image acquisition device comprising an objective lens and a sensing element having pixels, and wherein each image in the set is shifted from other images in the set by less than one half a size of a pixel of the sensing element;
reconstructing an image of the probe array using the set of micro-shifted images, wherein reconstructing the image comprises:
creating a single image from the set of micro-shifted images by taking a pixel from a common location within each of the micro-shifted images and tiling the pixels in the single image according to the spatial orientation corresponding to the shift direction and magnitude used during image acquisition, and repeating for each pixel associated with the set of micro-shifted images; and
creating an unboxed image from the single image, wherein the unboxed image is made up of subpixels defined by the shifts used to produce the micro-shifted images, and wherein creating the unboxed image comprises solving a system of linear algebraic equations to determine the value of each subpixel from the values of the pixels in the single image; and
deriving intensity values for one or more probe features on the region of the probe array from a reconstructed image, wherein the reconstructed image is created from at least one of the unboxed image or a deconvolved image.

2. The method according to claim 1, wherein each image in the set of micro-shifted images is shifted in increments of (1/N)*PixelSize, where N is any integer greater than 2.

3. The method according to claim 1, wherein a fixed spatial relationship is maintained between the probe array and the objective lens during image acquisition.

4. The method according to claim 3, wherein acquiring the set of micro-shifted images comprises shifting an element of the objective lens relative to the positions of the objective lens and the sensing element.

5. The method according to claim 3, wherein acquiring the set of micro-shifted images comprises shifting an element of the sensing element.

6. The method according to claim 1, wherein reconstructing the image further comprises creating the deconvolved image by using the single image as the starting image, the unboxed image as the initial guess, and a point spread function of the image acquisition device.

7. The method according to claim 6, wherein the deconvolved image is created using the Richardson-Lucy algorithm.

8. The method according to claim 7, further comprising using the Richardson-Lucy with Total Variation Regularization algorithm which has been modified to use, on a per iteration basis, parameters alpha, which includes over-relaxation or acceleration, and beta, which includes momentum.

9. The method according to claim 1, wherein the probe array comprises molecules labeled with semiconductor nanocrystals.

10. A method for obtaining an image, comprising:
providing a probe array in an image acquisition device comprising an objective lens, a shift element, and a sensing element having pixels;
acquiring an image of the probe array;
moving the shift element such that the image as observed at the sensing element shifts by less than one half the size of a pixel of the sensing element, while maintaining a fixed spatial relationship between the probe array and the objective lens of the image acquisition device;
acquiring a second image of the probe array;
repeating as necessary, in both X and Y dimensions, to produce a set of micro-shifted images;
reconstructing an image of the probe array using the set of micro-shifted images, wherein reconstructing the image comprises:
creating a single image from the set of micro-shifted images by taking a pixel from a common location within each of the micro-shifted images and tiling the pixels in the single image according to the spatial orientation corresponding to the shift direction and magnitude used during image acquisition, and repeating for each pixel associated with the set of micro-shifted images; and
creating an unboxed image from the single image, wherein the unboxed image is made up of subpixels defined by the shifts used to produce the micro-shifted images, and wherein creating the unboxed image comprises solving a system of linear algebraic equations to determine the value of each subpixel from the values of the pixels in the single image; and
deriving intensity values for one or more probe features on the region of the probe array from the reconstructed image, wherein the reconstructed image is created from at least one of the unboxed image or a deconvolved image.

11. The method according to claim 10, wherein each image in the set of micro-shifted images is shifted in increments of (1/N)*PixelSize, where N is any integer greater than 2.

12. The method according to claim 10, wherein reconstructing the image further comprises creating the deconvolved image by using the single image as the starting image, the unboxed image as the initial guess, and a point spread function of the image acquisition device.

13. The method according to claim 12, wherein the deconvolved image is created using the Richardson-Lucy algorithm.

14. The method according to claim 13, further comprising using the Richardson-Lucy with Total Variation Regularization algorithm which has been modified to use, on a per iteration basis, parameters alpha, which includes over-relaxation or acceleration, and beta, which includes momentum.

15. The method according to claim 10, wherein the probe array comprises molecules labeled with semiconductor nanocrystals.

16. A method for obtaining an image, comprising;
acquiring an image of a nucleic acid probe array using an image acquisition device comprising a CCD camera, an objective lens, and a tube lens;
translating the tube lens relative to the CCD camera such that the image of the nucleic acid probe array at the CCD camera is shifted by less than one half a pixel size of the CCD camera;
acquiring a second image of the nucleic acid probe array;
repeating as necessary to produce a set of micro-shifted images;
reconstructing an image of the nucleic acid probe array using the set of micro-shifted images, wherein reconstructing the image comprises:
creating a single image from the set of micro-shifted images by taking a pixel from a common location within each of the micro-shifted images and tiling the pixels in the single image according to the spatial orientation corresponding to the shift direction and magnitude used during image acquisition, and repeating for each pixel associated with the set of micro-shifted images; and
creating an unboxed image from the single image, wherein the unboxed image is made up of subpixels defined by the shifts used to produce the micro-shifted images, and wherein creating the unboxed image comprises solving a system of linear algebraic equations to determine the value of each subpixel from the values of the pixels in the single image; and deriving intensity values for one or more probe features on the region of the nucleic acid probe array from the reconstructed image, wherein the reconstructed image is created from at least one of the unboxed image or a deconvolved image.

17. The method according to claim 16, wherein each image in the set of micro-shifted images is shifted in increments of (1/N)*PixelSize, where N is any integer greater than 2.

18. The method according to claim 16, wherein reconstructing the image further comprises creating the deconvolved image by using the single image as the starting image, the unboxed image as the initial guess, and a point spread function of the image acquisition device.

19. The method according to claim 18, wherein the deconvolved image is created using the Richardson-Lucy algorithm.

20. The method according to claim 19, further comprising using the Richardson-Lucy with Total Variation Regularization algorithm which has been modified to use, on a per iteration basis, parameters alpha, which includes over-relaxation or acceleration, and beta, which includes momentum.

21. The method according to claim 1, wherein creating the unboxed image further comprises solving the system of linear algebraic equations using least squares or matrix notation.

* * * * *